(12) United States Patent
Bernstein

(10) Patent No.: US 9,056,072 B2
(45) Date of Patent: Jun. 16, 2015

(54) HORMONE NORMALIZATION THERAPY COMPRISING ADMINISTRATION OF AROMATASE INHIBITOR, FOLLICLE STIMULATING HORMONE, LUTEINIZING HORMONE, HUMAN CHORIONIC GONADOTROPIN, GONADOTROPIN HORMONE RELEASING HORMONE AND/OR PROGESTERONE

(76) Inventor: Lori R. Bernstein, Montgomery Village, MD (US)

(*) Notice: Subject to any disclaimer, the term of this patent is extended or adjusted under 35 U.S.C. 154(b) by 198 days.

(21) Appl. No.: 12/291,639

(22) Filed: Nov. 12, 2008

(65) Prior Publication Data

US 2009/0137478 A1    May 28, 2009

Related U.S. Application Data

(63) Continuation-in-part of application No. PCT/US2008/006021, filed on May 12, 2008.

(60) Provisional application No. 60/928,713, filed on May 11, 2007.

(51) Int. Cl.
*A61K 38/09* (2006.01)
*A61K 38/24* (2006.01)

(52) U.S. Cl.
CPC .......... *A61K 38/09* (2013.01); *G01N 2800/367* (2013.01); *A61K 38/24* (2013.01)

(58) Field of Classification Search
None
See application file for complete search history.

(56) References Cited

PUBLICATIONS

Ziegler et al., J Steroid Biochem Mol Biol. 2005; 95: 121-127.*
Montfrans et al., Human Reprod., 2004; 19: 430-434.*
Filicori et al., Human Reproduction Update, 2002; 8: 543-557.*
Balasch et al., Am J Obstet Gynecol. 1996; 175: 1226-30.*
Creus et al., Human Reproduction, 2000; 15: 2341-2346.*
Ziegler et al., Fertil Steril. 1991; 56: 851-855.*
Nakamura et al., Fertil Steril. 1986; 46: 46-54.*
Savage et al., Human Molecular Genetics, 1998; 7: 1221-1227.*

* cited by examiner

*Primary Examiner* — Christina Borgeest
(74) *Attorney, Agent, or Firm* — Benjamin Aaron Adler

(57) ABSTRACT

The present invention discloses a novel method of prevention of birth defects, miscarriages and infertility in women. The two therapies, disclosed herein, the hormone normalization therapy and the aromatase inhibitor-hormone normalization therapy, focus on restoring young hormonal levels in women in order to prevent female infertility and miscarriages, guide follicular and oocyte maturation, and promote correct chromosomal segregation in oocytes and early embryos.

23 Claims, 10 Drawing Sheets

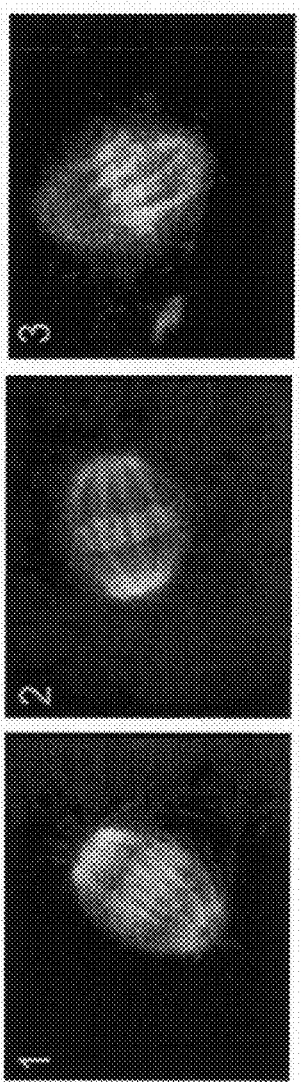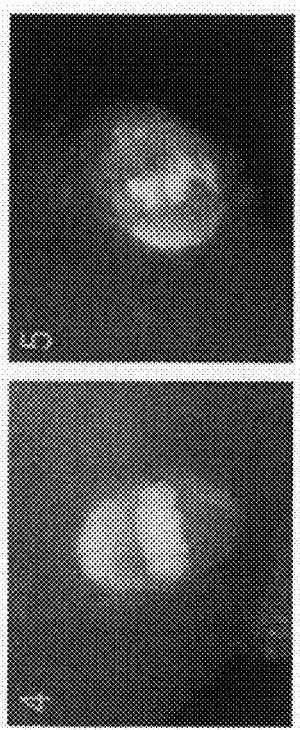

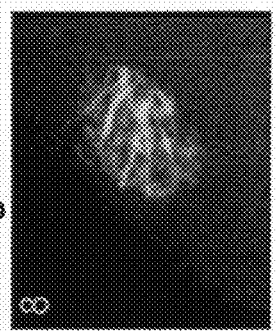
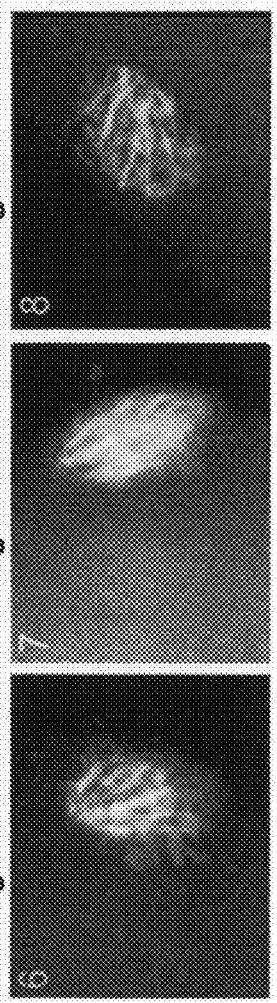
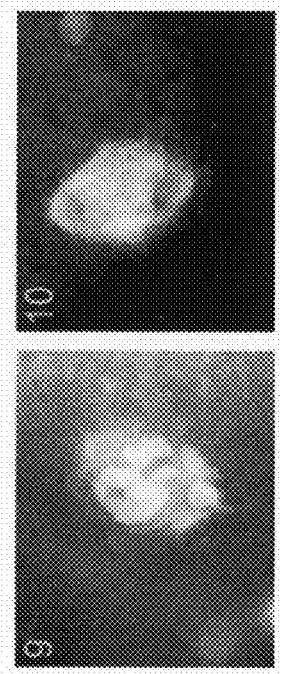
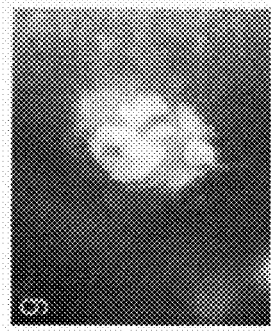
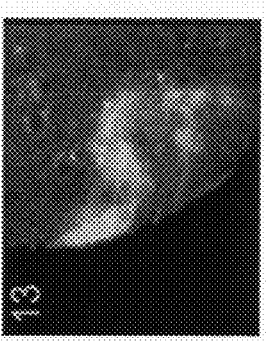
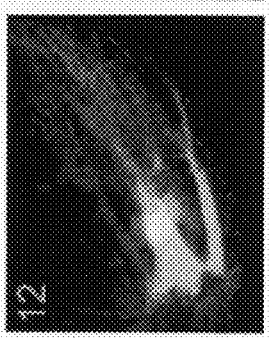
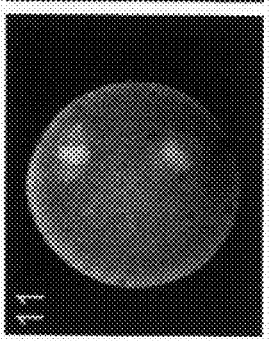

HORMONE NORMALIZATION THERAPY COMPRISING ADMINISTRATION OF AROMATASE INHIBITOR, FOLLICLE STIMULATING HORMONE, LUTEINIZING HORMONE, HUMAN CHORIONIC GONADOTROPIN, GONADOTROPIN HORMONE RELEASING HORMONE AND/OR PROGESTERONE

CROSS-REFERENCE TO RELATED APPLICATIONS

This is a continuation-in-part of International Application PCT/US2008/006021, with an international filing date of May 12, 2008, now abandoned, which claims priority under 35 U.S.C. §119(e) to provisional application U.S. Ser. No. 60/928,713, filed May 11, 2007, now abandoned.

BACKGROUND OF THE INVENTION

1. Field of the Invention

The present invention relates to the fields of reproductive biology and reproductive endocrinology. More specifically, the present invention discloses a hormone normalization therapy and its use in the prevention of infertility, miscarriages, stillbirths, and birth defects.

2. Description of the Related Art

Incidences of infertility, trisomic birth defects, and miscarriage undergo marked increases in women as they age (FIGS. 1A-1B). Women over the age of 35 are particularly vulnerable to these adverse reproductive outcomes. Nonetheless, the birth rates among women of advanced maternal age have increased significantly over the past 25 years because the average age for women to attempt to have a baby has increased dramatically (FIG. 2). Women aged 35 and older ("advanced maternal age" or "AMA") gave birth to 586,000 babies in the U.S. in 2004. This trend is particularly evident in westernized societies where education and career opportunities often delay marriage and childbearing. In Canada, for example, there has been an 83% increase in the number of babies born to advanced maternal age women just in the period of 1991 to 2000.

The delay in childbearing seen in the U.S., Canada, Europe, and Japan puts an increasingly greater number of women at risk of infertility, miscarriages and birth defects The combination of increased risk of infertility and pressure to have children later in life means that that these women are trying much harder to have babies than they did in the past. Based on conservative estimates obtained from statistics at the U.S. Government Census Bureau, there are 2,620,500 infertile American women aged 35-39, and 6,376,000 infertile women aged 40-44 (United States National Population Estimates, 2000-2005). An increasing percentage of women in this age group want to have a baby, but they cannot get pregnant. In addition, 127,000 US pregnancies per year for women over 35 are miscarried, out of 713,000 pregnancies. Although modern medicine has extended life expectancy, there have been no therapeutic advances to prevent chromosomal abnormalities from occurring when a woman uses her own eggs. Amniocentesis and other chromosomal abnormality tests lead to elective abortion of thousands of fetuses with trisomic birth defects. Some parents choose to continue their pregnancy and give birth to children with serious trisomic birth defects.

A primary cause of infertility, miscarriages and birth trisomic pregnancies is aneuploidy in the conceptus due to errors of chromosome segregation in the oocyte during meiosis. These errors create a fertilized embryo that has an extra copy of a given chromosome (trisomy), or just one copy of that chromosome (monosomy). The increase in miscarriage rates in AMA women is primarily attributable to trisomic conceptions. Whereas only 8% of embryos from women in their early to mid 20s are chromosomally abnormal, 84% of embryos from women 35-39 are chromosomally abnormal, as are nearly all embryos from women over 40.

Greater than 90% of miscarriages and a large percentage of the increased incidence of infertility with age are caused by chromosomal and genetic errors in the embryo. Monosomic conceptions manifest as infertility. Trisomic conceptions manifest as infertility, miscarriages, stillborns, or birth defects, depending on the identity of the malsegregated chromosome. Trisomies 21, 18, and 13 cause Down, Edward and Patau syndromes, respectively.

Advanced maternal age women often display significantly elevated follicle stimulating hormone (FSH) and/or 17-bE-stradiol (E2) levels during their menstrual cycles, compared to younger women. The menstrual cycles of advanced maternal age women, particularly the follicular phases, are significantly shorter than those of young women. The luteinizing hormone (LH) surge occurs much earlier in advanced maternal age women than in younger women.

Gonadotropin and steroid hormones are potent regulators of the developmental events occurring in follicular cells and oocytes that terminate in meiosis and ovulation. A number of studies have shown that FSH, E2 and LH work in concert to orchestrate follicular development and many processes in the oocyte, including meiotic maturation and progression, nuclear and cytoplasmic maturation, centrosomal and cytoskeletal organization, and the resumption of meiosis. Changes in the intrafollicular microenvironment caused by perturbations in levels of FSH and E2, and changes in the timing of follicular and oocyte maturation relative to changes in gonadotropin and steroid hormone levels across the cycle caused by a short follicular phase, can significantly compromise the developmental integrity and timed meiotic progression of the follicle and the oocyte.

High FSH and E2 are associated with increased incidences of infertility, miscarriages, and aneuploid conceptuses in animals and in women. A short menstrual cycle length and follicular phase in women are also associated with infertility and miscarriages in women. High levels of exogenously administered FSH, E2, and other estrogenic compounds have been shown in a number of studies to cause spindle disruption, chromosome disorganization, aneuploid conceptions, and pregnancy losses. Since gonadotropin and steroid hormones control the fine-tuned processes that orchestrate meiotic maturation and progression, and since exogenously administered FSH and E2 cause aneuploidy, elevated endogenous FSH and E2 likely contribute to aneuploidy in advanced maternal age women.

Trisomy of chromosome 21 causes Down syndrome, a severe condition characterized by mental retardation, susceptibility to infection, cardiac defects, a high incidence of Alzheimer's dementia, and a short lifespan. Several other chromosomes also experience chromosome segregation problems with increased frequency in advanced maternal age. Trisomies of chromosome 18 and chromosome 13 cause Edward and Patau syndromes, respectively, two extremely severe birth defects that cause mental retardation and cardiac defects, and are fatal within several weeks or months of birth. Most Down syndrome babies (80% of all conceived babies with Down syndrome) as well as babies with Patau and Edward's syndromes are not born alive because they fail to make it to term or they are stillborn. Trisomies of a variety of other chromosomes (predominantly 14, 15, 16, 22) cause miscarriages in many patients, and a number of other trisomies as well as monosomic conceptions are lethal in the peri-implantation period and manifest as infertility. Trisomic birth defects, stillbirths, miscarriages, and infertility caused by aneuploidy create profound suffering for parents, their offspring, and the immeasurable loss of those children who were not born.

Thus, the prior art is deficient in therapies designed to prevent infertility, miscarriage and trisomic birth defects caused by aneuploidy. The present invention fulfills this long-standing need and desire in the art.

SUMMARY OF THE INVENTION

There are no current therapies that prevent the occurrence of chromosomal abnormalities in oocytes and embryos of women of advanced maternal age. Preimplantation genetic diagnosis (PGD) biopsies for chromosomal abnormalities prior to implanting an embryo have been created through in vitro fertilization. However, PGD has no demonstrable value for preventing infertility caused by age-related aneuploidy, and its effectiveness for preventing miscarriages for women with recurrent spontaneous abortions is in dispute. Furthermore preimplantation genetic diagnosis does not cure the underlying egg quality problem in advanced maternal age women; it only allows abnormal embryos to be discarded prior to implantation. Hence, the present invention discloses methods that allow the eggs of an older woman to develop normally. This prevents chromosomal abnormalities associated with advanced maternal age that contribute to infertility, miscarriages and trisomic birth defects.

The present invention is directed to a method of reducing the incidence of infertility, miscarriage, and/or trisomic stillborns and liveborns in a woman in need of such treatment. Such a method comprises regulating levels of follicle stimulating hormone (FSH), estrogen, luteinizing hormone activity, estradiol and progesterone in the woman such that the levels become similar to the levels of follicle stimulating hormone of a young and fertile woman, thereby reducing the incidence of infertility, miscarriage and/or trisomic stillborns and liveborns in the woman. The present invention is directed to a related method further comprising regulating levels of estradiol in the woman such that the levels become similar to the levels of estradiol in the young and fertile woman.

The present invention is also directed to another method for reducing the incidence of infertility, miscarriage, and/or trisomic stillborns and liveborns in a woman in need of such treatment. Such a method comprises regulating levels of follicle stimulating hormone to approximate varying serum levels of follicle stimulating hormone that exist in a young and fertile woman throughout the menstrual cycle of the woman. It is also comprised of luteinizing hormone activity to support follicular and oocyte maturation and to trigger ovulation, and of progesterone to support the luteal phase in the woman. Additionally, an inhibitor of the enzyme aromatase is administered such that the above-mentioned regulations and the administration of the inhibitor regulates level of estradiol such that the level approximates the level of estradiol of a young and fertile woman. The described invention reduces the incidence of infertility, miscarriage and/or trisomic liveborns in the woman.

The present invention is also directed to a kit. Such a kit comprises a gonadotropin releasing hormone (GnRH), a gonadotropin releasing hormone agonist, and/or a gonadotropin releasing hormone antagonist; a follicle stimulating hormone preparation; a luteinizing hormone preparation and/or a human chorionic gonadotropin preparation; a progesterone preparation; and instructions for administration.

Alternatively, the present invention is directed to a kit that comprises a gonadotropin releasing hormone, a gonadotropin releasing hormone agonist or a gonadotropin releasing hormone antagonist, a follicle stimulating hormone preparation, a luteinizing hormone preparation and/or a human chorionic gonadotropin preparation, a progesterone preparation, an aromatase inhibitor; device(s) for drug administration; and instructions for administration.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 3C) compared to young women (bottom). Note that the differences in hormonal levels between young and AMA women are more pronounced between AMA women with infertility, birth defective conceptuses, or history of recurrent pregnancy losses vs. young women, than they are between the general population of AMA women vs. young women.

FIGS. 7A-7M show that chromosomes and spindles in oocytes from old 7 months SAM8 mice (FIGS. 7A-7E) are more disorganized than chromosomes and spindles in oocytes from young 2.5 months SAM8 mice (FIGS. 7F-7M). FIGS. 7A-7C, 7F-7H and 7K-7M depict meiosis I oocytes. FIGS. 7D-7E and 7I-7J depict meiosis II oocytes. In FIGS. 7A-7E the oocytes have organized chromosomes and spindles while in FIGS. 7F-7M the oocytes have disorganized chromosomes and spindles. In FIGS. 7H and 7L-7M the oocytes have chromosome and spindle abnormalities. In FIG. 7K the oocyte has two sets of chromosomes and spindles.

DETAILED DESCRIPTION OF THE INVENTION

As used herein, the abbreviations AMA, HNT, E2, FSH, LH, P4, GnRH, AI, AI-HNT, DOR, BMI, IUI, IVF, FISH, sc, CGH, RIF, IM mean respectively: Advanced Maternal Age, Hormone Normalization Therapy, estradiol, follicle stimulating hormone, luteinizing hormone, progesterone, gonadotropin releasing hormone and aromatase inhibitor, aromatase inhibitor hormone normalization therapy, diminished ovarian reserve, intrauterine insemination, in vitro fertilization, fluorescence in-situ hybridization, subcutaneous, comparative genomic hybridization, recurrent implantation failure, intramuscular.

Figure 1B:
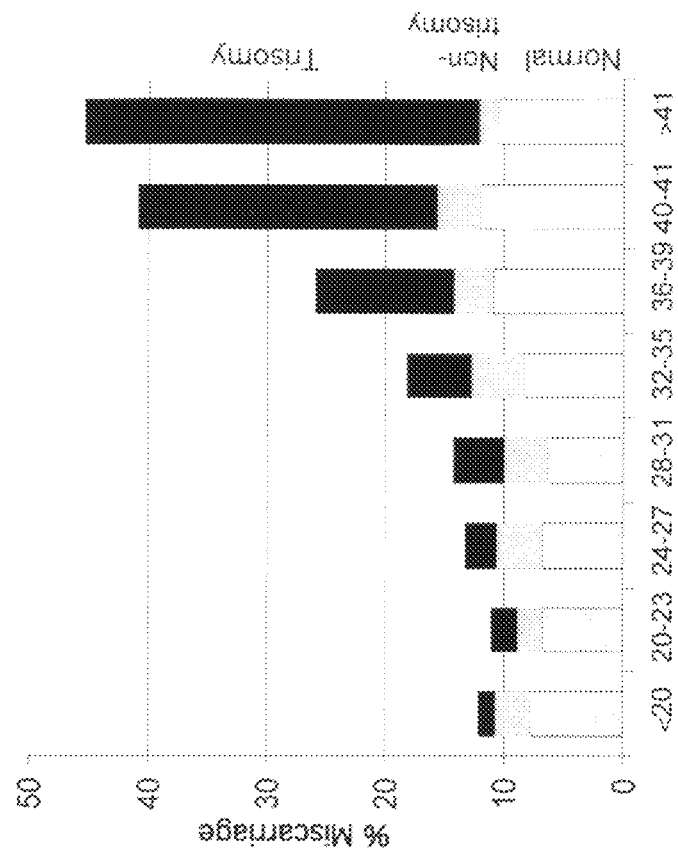
FIGS. 1A-1B illustrate that fertility plummets and miscarriage rates increase with age (FIG. 1A) and that the increase in miscarriage rates with age is primarily due to increased rates of trisomy in the conceptus (FIG. 1B). Solid black: trisomic miscarriages; Grey: other chromosomally abnormal miscarriages; Striped: chromosomally normal miscarriages.
Figure 1A:
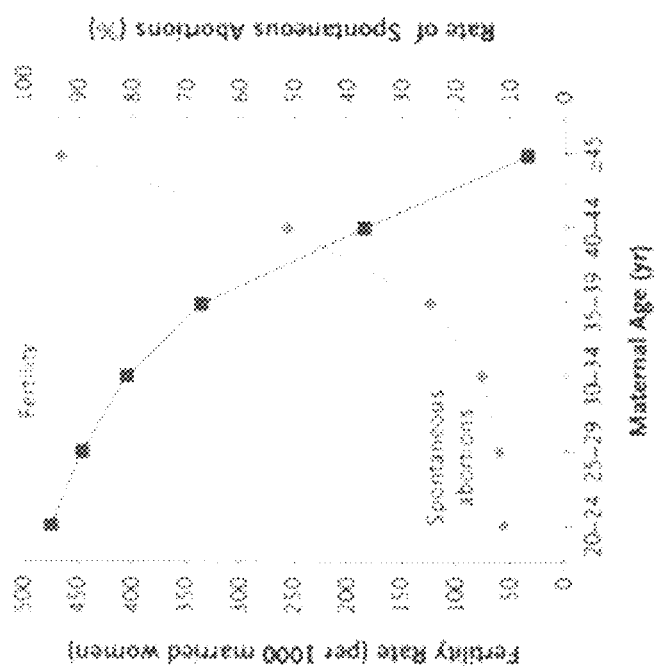
Figure 2:
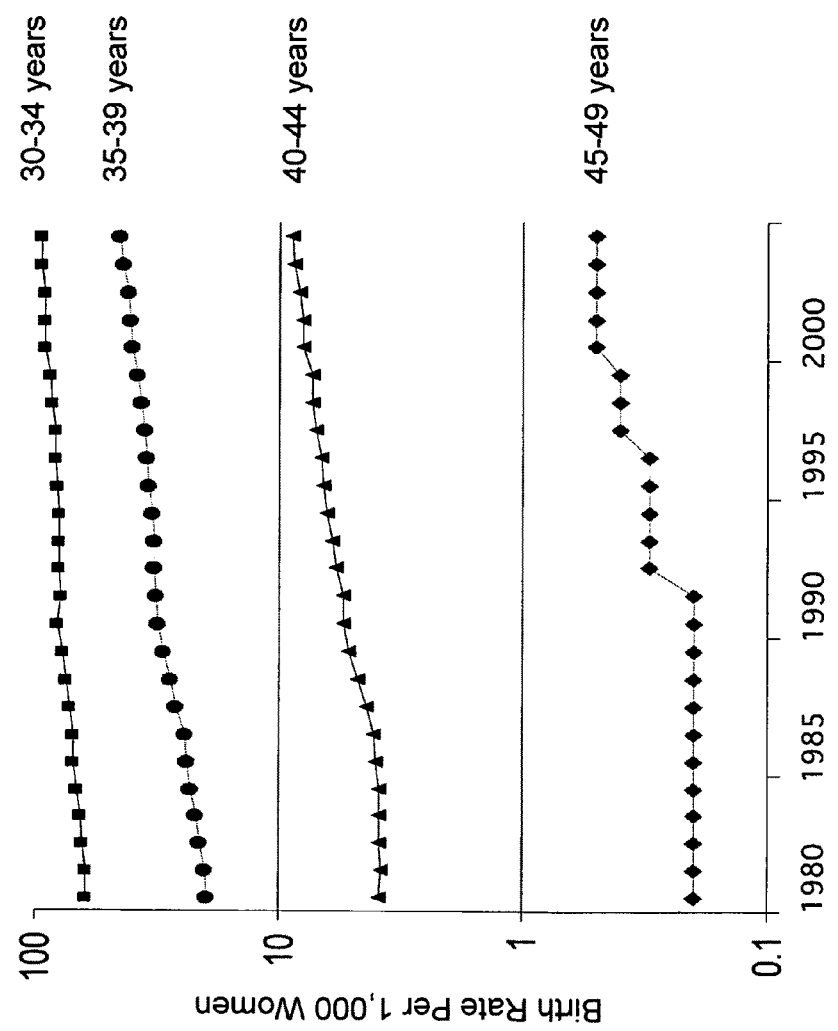
FIG. 2 shows birth rates in older women have been increasing significantly.
Figures 3A, 3B:
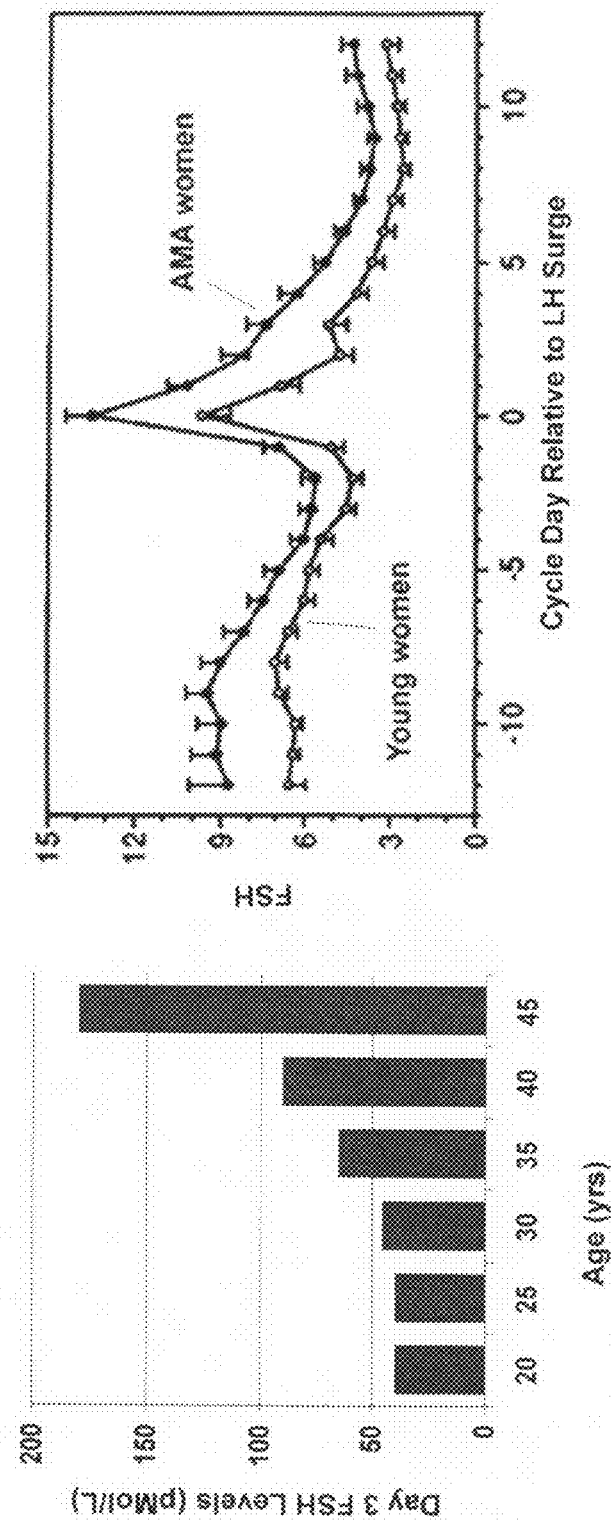
FIGS. 3A-3C show that as a general population, advanced maternal age (AMA) women (top) have elevated levels of FSH (FIGS. 3A-3B) and estradiol (E2.
Figure 3D:
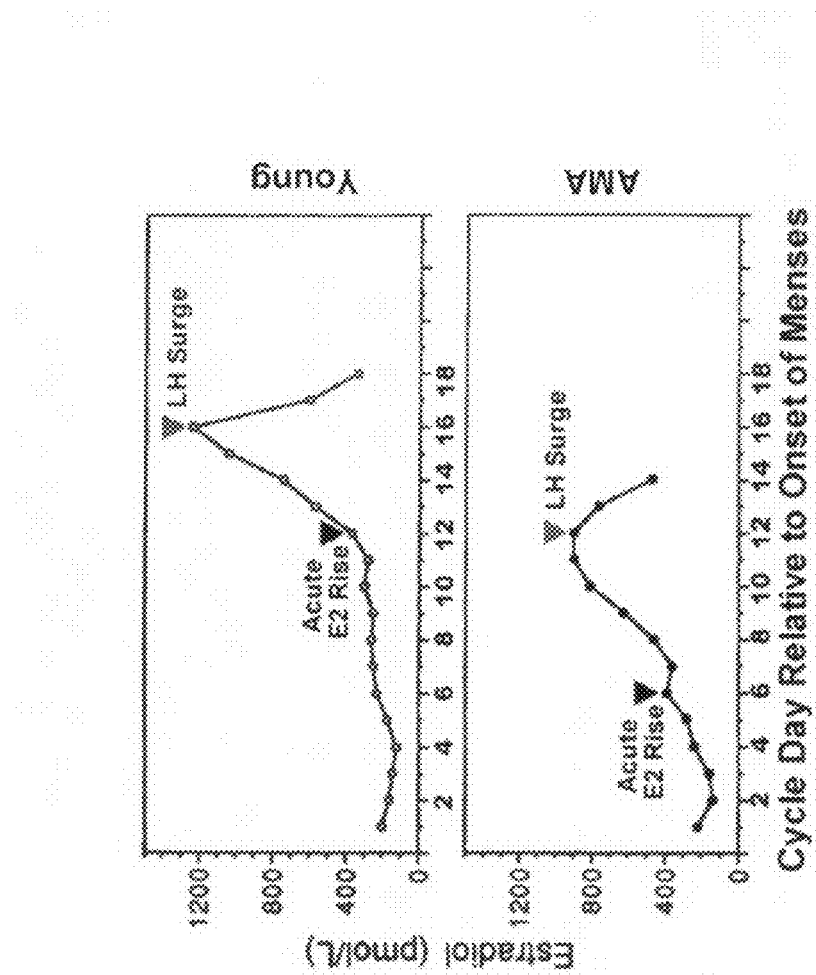
FIG. 3D shows prototypical patterns of follicular phase lengths in a young woman, age 22, versus an AMA woman, age 44, illustrating that AMA women have much shorter follicular phases with an early rise in E2 and an early LH surge. At day 3 of the cycle 5.8 mIU/ml FSH and 9.2 mIU/ml FSH were administered to the young and AMA women, respectively
Figure 3C:
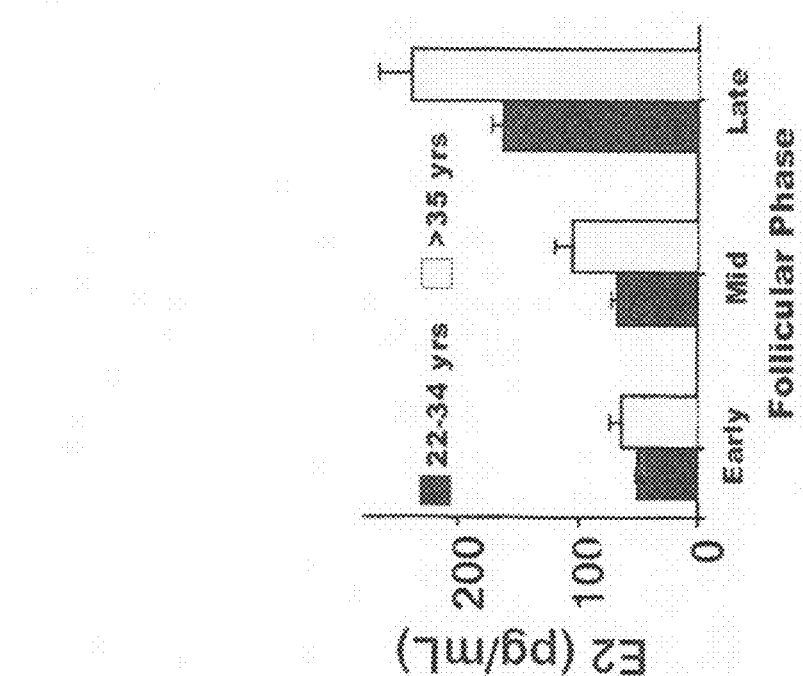

Although there are a number of causes of infertility and miscarriages, oocyte aneuploidy is a major contributing factor, especially among women of advanced maternal age. A critical pathway by which hormone normalization therapy will improve female fertility is by the prevention of aneuploidy. Numerous papers have been published demonstrating an association between high endogenous hormonal levels of FSH or E2, and infertility, and oocyte or embryo aneuploidy; and between elevated FSH or E2, and spontaneous abortion and oocyte or embryo aneuploidy. Other papers in the literature have shown that high levels of exogenously administered follicle stimulating hormone (FSH) or of estradiol (E2) cause aneuploidy in the oocytes and embryos of animals and humans. Furthermore, it is well established that women of advanced maternal age have elevated levels of FSH and/or E2, and a short follicular phase (FIGS. 3A-3C). Therefore it is logical that elevated FSH and E2 and the shortened follicular phase that normally occur as women age cause aneuploidy in oocytes and embryos. The instant invention refers to this as "hormonal aging" (FIG. 3D).

The notion that hormone levels in women cause oocyte aneuploidy has been largely discarded by obstetricians and gynecologists. Two theories have received widespread acceptance to explain the causes of advanced maternal age aneuploidy. One theory is that advanced maternal age oocytes display high incidence of aneuploidy due to incremental deterioration and environmental (primarily oxidative) damage that occurs during the extended time during which the oocyte is suspended in meiotic prophase prior to ovulation (35 or more years for an advanced maternal age woman). Another theory is that within the female reproductive lifespan, the oocytes of the best quality are ovulated first, and those of the lowest quality are ovulated last.

If either of these theories is correct, then an inexorable decline in oocyte viability accompanies the aging process, and there is no evident cure for the decline in oocyte quality that occurs as a woman ages. Donor eggs are the only recourse for these patients. However, if hormonal aging accounts for some, if not all effects, then it is possible to reduce the incidence of aneuploidy and infertility by restoring the hormonal milieu in an advanced maternal age woman to that of a young woman.

In previous studies, exogenous administration of estrogenic compounds and FSH has been demonstrated to cause spindle disruption and chromosome disorganization in oocytes. These data support the hypothesis that hormonal aberrations that normally accompany the aging process play an important role in causing meiotic non-disjunction errors in the oocyte. The present invention predicts that it should be possible to prevent chromosomal non-disjunction by a therapeutic hormone regimen designed to optimize the levels of circulating gonadotropin and steroid hormones to those of a young women during the menstrual cycle.

Hormone normalization therapy uses drugs that have been used safely in humans in combination with one another in hundreds of thousands of patients for many years in controlled ovarian hyperstimulation (COHS), both for intrauterine insemination (IUI) and in vitro fertilization (IVF) protocols. Gonadotropin releasing hormone (GnRH), GnRH agonists or antagonists; FSH preparations; luteinizing hormone activity preparations containing human chorionic gonadotropin (hCG) or luteinizing hormone (LH); and progesterone as needed, are the hormones to be administered and a part of the kit of the present invention. However, the dosages and the duration of the therapy are markedly different than COHS protocols. Much lower doses of FSH are used in hormone normalization therapy than in controlled ovarian hyperstimulation, and the hormones are given to the patient in a cyclical modality, for example, preferably 34 months, versus a set of much higher dose injections of FSH given to COHS patients over a much briefer period. A monthly cyclical modality may comprise, inter alia, 2, 3 or 4 months. It is contemplated that the level of response among treated women will vary and those responding quicker may become pregnant within a shorter period of time. Levels of FSH are much more closely controlled and varied in HNT than in COHS at all points of the cycle. FSH and GnRH, GnRH agonist, or GnRH antagonist administration includes the luteal phase of the cycle, unlike controlled ovarian hyperstimulation, during which FSH and GnRH, GnRH agonist, or GnRH antagonist are administered only during the follicular phase of the cycle.

Additional control of E2 levels is afforded using treatments with aromatase inhibitor, again employing much lower dosages of AI than are utilized by reproductive endocrinologists currently.

In addition to preventing miscarriages and birth defective conspectuses, hormone normalization therapy can also permit the birth of babies to women of advanced maternal age with idiopathic infertility or diminished ovarian reserve (DOR), as well as those undergoing premature ovarian failure (POF) who only have minimal remaining ovarian reserve. Women with repeated implantation failure ("RIF") after in vitro fertilization are also candidates for this therapy.

A significantly shortened follicular phase is a hallmark of reproductive aging in women, and it is correlated with reduced fertility and increased incidence of miscarriages. Disruptions in the cyclic timing of hormonal changes relative to the timing of oocyte maturation and ovulation may predispose the oocyte to aneuploidy during meiosis. To prevent infertility and miscarriages associated with a shortened follicular phase, hormone normalization therapy will be performed during which the duration of the follicular phase will be increased to that of a young and fertile woman.

The present invention is demonstrated at least in part using a three-pronged approach: studies in mice, primates, and humans. Initial studies in mice have identified two strains of mice that serve as good models for ovarian aging and advanced maternal age aneuploidy. HNT studies will be performed with these mouse strains. These studies consist of GnRH-agonist downregulation of advanced maternal age mice followed by administration of FSH, to approximate the FSH levels of a young mouse throughout the estrous cycle, so as to reduce the incidence of oocyte and embryo aneuploidy in the old female mice. Ovulation will be triggered by LH activity, and progesterone will be administered in order to emulate cyclic changes in progesterone levels that occur in the mouse estrus cycle. A reverse protocol, called hormone de-normalization therapy (HDT) is also performed, in which young mice are subjected to the reproductive hormonal profile of old mice, to demonstrate that the young hormone de-normalization therapy-treated mice exhibit increased incidence of aneuploidy like that of their older counterparts. For nonhuman primates, several species are evaluated, using the same criteria for a good model. Good candidates include the baboon, the cynomologous macaque, the rhesus macaque, and the marmoset monkey. The species that best fulfills the criteria are subject to hormone normalization therapy studies. Hormone de-normalization therapy is also performed.

Two types of human clinical trials are performed, an "aneuploidy trial" and a "pregnancy trial." In the aneuploidy trial, oocytes from advanced maternal age women are retrieved from patients in the cycle prior to the first hormone normalization therapy cycle, and polar bodies are biopsied from IVF embryos derived from oocytes after the completion of the final hormone normalization therapy cycle. Drug therapy in this trial occurs throughout the follicular and luteal phases of the cycles that precede the retrieval in the actual test cycle, and throughout the follicular phase of the cycle in which the oocyte retrieval occurs. Unfertilized oocytes retrieved before the commencement of HNT, and polar bodies from embryos generated by IVF after HNT are analyzed by comparative genomic hybridization (CGH) or by multicolor fluorescence in-situ hybridization (FISH) to demonstrate decreased aneuploidy after hormone normalization therapy. In the pregnancy trial patients will undergo hormone normalization therapy during the follicular and luteal phases of the cycles that precede the actual test cycle, and continue drug treatment throughout the follicular phase of the test cycle, when the patients undergo insemination with male partner's sperm to demonstrate improved pregnancy rates, lower miscarriage rates, and higher live birth rates.

Further, in an alternative protocol of the present invention, the hormone normalization therapy is supplemented by the addition of an inhibitor of the enzyme aromatase to the hormone normalization therapy protocol. The aromatase inhibitors used in HNT inhibit the enzyme aromatase, which catalyzes the biosynthesis of estradiol from testosterone. Aromatase inhibitors are FDA approved drugs that are widely used for treatment of early stage metastatic estrogen receptor positive breast cancers. The catalytic activity of the enzyme aromatase is induced by FSH and other regulators. Aromatase inhibitors lower the body's production of estradiol by inhibiting the aromatase enzyme that is present in ovarian follicles and other tissues. The aromatase inhibitor improvement is referred to as "Aromatase inhibitor-hormone normalization therapy" (AI-HNT) in the present invention. Aromatase inhibitor-hormone normalization therapy is specifically designed to help patients with a history of recurrent miscarriage, birth defective conceptions, or infertility who have elevated serum estradiol levels compared to young women.

In addition to treating women to prevent miscarriages and birth defective conceptuses, aromatase inhibitor-hormone normalization therapy is used to help advanced maternal age women with high estradiol and idiopathic infertility, diminished ovarian reserve (DOR), or premature ovarian failure (POF) who still have some minimal remaining ovarian reserve. Women with high estradiol and repeated implantation failure ("RIF") after in vitro fertilization (IVF) are also candidates for this therapy. Aromatase inhibitors afford an additional advantage of controlling estradiol levels to a degree that has previously been impossible. The control over estradiol levels that are afforded by aromatase inhibitors may make the difference between a successful pregnancy attempt and an unsuccessful one in many cases.

In one embodiment of the present invention there is provided a method of reducing the incidence of infertility, miscarriage, and/or trisomic stillborns and liveborns to a woman in need of such treatment, comprising regulating levels of follicle stimulating hormone, luteinizing hormone, and progesterone in the woman such that the levels of follicle stimulating hormone become similar to the levels of follicle stimulating hormone and estradiol Further to this embodiment the method comprises regulating levels of estradiol in the woman such that the levels are similar to the levels of estradiol in the young and fertile woman. For example, an inhibitor of the aromatase enzyme may be administered, such as are described infra. This regulation of hormonal levels reduces the incidence of infertility, miscarriage, and/or trisomic stillbirths and/or liveborns in the woman. The levels of follicle stimulating hormone, luteinizing hormone, estrogen, and progesterone may be regulated in the woman by reducing pituitary secretion of follicle stimulating hormone and luteinizing hormone, attenuating ovarian secretion of estrogen and progesterone; and by administering follicle stimulating hormone at various doses throughout the menstrual cycle to achieve the various at levels of FSH in young and fertile woman at each stage of the menstrual cycle. This may be supplemented by adding supplementary LH or hCG to assist in oocyte and follicular maturation; and with progesterone as needed for luteal phase support. The pituitary secretion of follicle stimulating hormone and luteinizing hormone may be reduced by administrating a gonadotropin releasing hormone or an agonist of gonadotropin stimulating hormone and/or an antagonist of gonadotropin stimulating hormone. Examples of the agonist of gonadotropin releasing hormone may include but are not limited to Leuprolide, Buserelin, Goserelin, Histrelin, Leuprorelin, Nafarelin, Triptorelin, gonadorelin, fertirelin, or deslorelin and examples of antagonists of gonadotropin releasing hormone may include but are not limited to abarelix, cetrorelix, ganirelix, antarelix, iturelix (antide), Nal-glu, or orgalutran.

Further, the follicle stimulating hormone is administered as human menopausal gonadotropin, purified follicle stimulating hormone, and/or recombinant follicle stimulating hormone. Daily supplementation of the FSH treatment may be provided with luteinizing hormone activity in the form of luteinizing hormone (LH), human chorionic gonadotropin (hCG), or a combination thereof. hCG and/or LH are provided in a bolus injection to trigger ovulation. Furthermore, luteal phase progesterone may be administered as progesterone in oil for intramuscular injections; micronized progesterone capsules in oil comprised of prometrium, uteregestan, minagest or microgest for use as vaginal suppositories; bioadhesive vaginal gels comprising crinone or prochieve, and custom compounded vaginal suppositories. Prometrium, uteregestan, minagest or microgest capsules can also be used as optional additional supplementation in conjunction with vaginal delivery, as an orally delivered progesterone treatment.

The regulation described supra may be carried out over at least two cycles, such as, but not limited to, 2, 3 or 4 cycles based on at least 50 days FSH responsiveness of growing follicle prior to ovulation to maximize therapeutic effectiveness. Such a regulation may be effective in normalization of menstrual cycle length, enhancing chances of successful full-term pregnancies without miscarriages, prevention of aneuploidy in oocytes and embryos; reducing infertility by other pathways promoted by hormonal regulation or a combination thereof. The normalization of menstrual cycle length may extend and thereby restore the duration of follicular phase of the woman to approximate that of a young and fertile woman. The approximation may be by administration of human menopausal gonadotropin, purified follicle stimulating hormone, and/or recombinant follicle stimulating hormone in the context of downregulation with GnRH, GnRH agonist, or GnRH antagonist, with or without supplementation with luteinizing hormone, and/or supplementation with hCG; triggering of ovulation with urinary hCG, recombinant hCG, highly purified hCG, or recombinant LH, or a combination thereof. Additionally, the woman may be infertile due to premature ovarian failure, repeated implantation failure after in vitro fertilization, diminished ovarian reserve (DOR), or idiopathic infertility. The woman may also have elevated follicle stimulating hormone level and normal estradiol level.

In another embodiment of the present invention there is provided a method for reducing the incidence of infertility, miscarriage, and/or trisomic stillborns and liveborns to a woman in need of such a treatment, comprising: regulating levels of follicle stimulating hormone so as to approximate those that exist in a young and fertile woman throughout menstrual cycle of the woman; supplementary luteinizing hormone activity to support follicular and oocyte maturation; luteinizing hormone activity to trigger ovulation; progesterone to support luteal phase in the woman; and co-administering an inhibitor of the enzyme aromatase such that the regulation and the administration regulates level of estradiol such that the level approximates the level of estradiol of a young and fertile woman, thereby reducing the incidence of infertility, miscarriage and/or trisomic stillborns and liveborns in the woman.

The pituitary secretion of follicle stimulating hormone will be reduced by administrating gonadotropin releasing hormone, an agonist of gonadotropin stimulating hormone or an antagonist of gonadotropin stimulating hormone to reduce pituitary secretion of follicle stimulating hormone and luteinizing hormone, and reduce ovarian secretion of estrogen and progesterone. Follicle stimulating hormone will then be increased by FSH administration to approximate hormonal levels that are specific for each stage of the menstrual cycle in a young and fertile woman, restoring levels of estradiol at levels that are specific for the stages of the menstrual cycle, and restoring progesterone at levels that are adequate for the luteal phase. Examples of the agonist and antagonist of gonadotropin releasing hormone are described supra. The follicle stimulating hormone may be restored by administration of human menopausal gonadotropin, purified follicle stimulating hormone, recombinant follicle stimulating hormone, with or without supplementation with luteinizing hormone, supplementation with human chorionic gonadotropin or a combination thereof. Furthermore, the progesterone level may be increased by administrating progesterone in oil for intramuscular injections; micronized progesterone capsules in oil comprised of prometrium, uteregestan, minagest or microgest for use as vaginal suppositories; bioadhesive vaginal gels comprising crinone or prochieve, and custom compounded vaginal suppositories. Prometrium, uteregestan, minagest or microgest capsules can also be used as optional additional supplementation in conjunction with vaginal delivery, as an orally delivered progesterone treatment; Examples of the aromatase inhibitor may include but are not limited to aminogluthetimide, anastrozole, exemestane, formestane, letrozole, vorozole, 4-androstene-3,6,17-trione, 1,4,6-androstatrien-3,17-dione, or testolactone.

The regulation may be carried out over at least two cycles, as described supra, to maximize therapeutic effectiveness. Additionally, the regulation may be effective in normalizing menstrual cycle length, enhancing chances of successful full term pregnancy without miscarriage in a woman with or without elevated estradiol, preventing aneuploidy in oocytes; reducing infertility by other pathways regulated by hormonal levels or a combination thereof. Further, the normalization of menstrual cycle length may restore the duration of the follicular phase of the woman to approximate that of a young and fertile woman. The approximation may be carried out by administrating human menopausal gonadotropin, purified follicle stimulating hormone, recombinant follicle stimulating hormone, or combination thereof, with or without supplementary urinary hCG, highly purified hCG, recombinant hCG or recombinant LH or a combination thereof; triggering of ovulation with urinary hCG, highly purified hCG, recombinant hCG or recombinant LH or a combination thereof; and luteal phase support with a preparation of progesterone as needed. The woman may be infertile due to premature ovarian failure, repeated implantation failure, diminished ovarian reserve, or idiopathic infertility. Furthermore, the woman may have elevated follicle stimulating hormone level and/or elevated estradiol level.

In yet another embodiment of the present invention there is provided a kit that comprises preparations of gonadotropin releasing hormone, gonadotropin releasing hormone agonist and/or a gonadotropin releasing hormone antagonist; a follicle stimulating hormone preparation; a luteinizing hormone activity preparation and/or a human chorionic gonadotropin preparation; a progesterone preparation; and instructions for administration. Examples of the gonadotropin releasing hormone agonist may include but are not limited to Leuprolide, Buserelin, Goserelin, Histrelin, Leuprorelin, Nafarelin, Triptorelin, gonadorelin fertirelin, or deslorelin and examples of antagonists of gonadotropin releasing hormone may include but are not limited to abarelix, cetrorelix, ganirelix, antarelix, iturelix (antide), or orgalutran. Further, the follicle stimulating hormone preparation may comprise but is not limited to human menopausal gonadotropin, purified follicle stimulating hormone, recombinant follicle stimulating hormone, supplementation with luteinizing hormone, and/or supplementation with human chorionic gonadotropin or a combination thereof. Additionally, the luteinizing hormone preparation or the human chorionic gonadotropin preparation may comprise but is not limited to urinary hCG, highly purified hCG, recombinant hCG or recombinant LH. Furthermore, the progesterone preparation may include but is not limited to progesterone in oil for intramuscular injections; micronized progesterone capsules in oil comprised of prometrium, uteregestan, minagest or microgest for use as vaginal suppositories; bioadhesive vaginal gels comprising crinone or prochieve, and custom compounded vaginal suppositories. Prometrium, uteregestan, minagest or microgest capsules can also be used as optional additional supplementation in conjunction with vaginal delivery as an orally delivered progesterone treatment.

In yet still another embodiment of the present invention there is a kit that comprises preparations of gonadotropin releasing hormone, gonadotropin releasing hormone agonist and/or a gonadotropin releasing hormone antagonist; a follicle stimulating hormone preparation; a luteinizing hormone activity preparation and/or a human chorionic gonadotropin preparation; a progesterone preparation; an aromatase inhibitor; and instructions for administration. Examples of the gonadotropin releasing hormone agonist may include but are not limited to Leuprolide, Buserelin, Goserelin, Histrelin, Leuprorelin, Nafarelin, Triptorelin, gonadorelin, fertirelin, or deslorelin and those of the gonadotropin releasing hormone antagonist may include but are not limited to abarelix, cetrorelix, antorelix, iturelix (antide), Nal-glu, orgalutran, or ganirelix. The follicle stimulating hormone preparation may comprise but is not limited to human menopausal gonadotropin, purified follicle stimulating hormone, recombinant follicle stimulating hormone, supplementation with luteinizing hormone, supplementation with human chorionic gonadotropin or a combination thereof. Similarly, the luteinizing hormone activity preparation or the human chorionic gonadotropin activity preparation may comprise but are not limited to urinary hCG, recombinant hCG, highly purified hCG, or recombinant LH. Furthermore, the progesterone level may include but is not limited to progesterone in oil for intramuscular injections; micronized progesterone capsules in oil comprised of prometrium, uteregestan, minagest or microgest for use as vaginal suppositories; bioadhesive vaginal gels comprising crinone or prochieve, and custom compounded vaginal suppositories. Prometrium, uteregestan, minagest or microgest capsules can also be used as additional supplementation in conjunction with vaginal delivery, as an orally delivered progesterone treatment; Furthermore, the examples of the aromatase inhibitor may include but are not limited to aminogluthetimide, anastrozole, exemestane, formestane, letrozole, vorozole, 4-androstene-3,6,17-trione, 1,4,6-androstatrien-3,17-dione, or testolactone.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Patient Groups

Women aged 35 and over are the initial subjects for these studies. Initial subjects will have high FSH, and/or high E2. They will have had 1 or more documented autosomal trisomic conceptus or 2 or more miscarriages may or may not have been karyotyped. This test group includes patients who have had Down, Patau, and Edward syndrome pregnancies. Subjects who will also be candidates for the therapy are patients with high FSH and/or E2 and a history of idiopathic infertility, premature ovarian failure, diminished ovarian reserve, or repeated implantation failure. Hormone normalization therapy has the potential to prevent a number of underlying defects. Additional criteria include normal Body Mass Index (BMI), Thyroid Stimulating Hormone (TSH), prolactin, maternal and paternal karyotypes, and uterine morphology; negative for thrombophilias associated with recurrent pregnancy loss and infertility.

EXAMPLE 2

Strategy of Hormonal Normalization Therapy

A fundamental objective of hormone normalization therapy is to restore young hormonal levels in advanced maternal age women in order to correct chromosomal segregation. The first central idea of hormone normalization therapy is to take control over the bodies' pituitary secretory function so that the body may be rid of ovarian exposure to chronically elevated levels of FSH. This is accomplished by downregulating pituitary secretion of FSH by daily injection of high levels of a gonadotropin releasing hormone (GnRH), or with a GnRH agonist or antagonist. LH is also downregulated in the course of the treatment. This treatment is performed for the duration of the hormone normalization therapy regimen, including during the luteal phases of the menstrual cycles that occur during the therapy, to achieve sustained pituitary downregulation throughout the duration of the therapy. The use of GnRH downregulation to achieve control over the hypothalamic-pituitary-ovarian (HPO) axis is important to the success of the protocol, and is a classic method in assisted reproductive technologies (ART).

A second central concept of hormone normalization therapy is to reconstitute the levels of reproductive hormones that are typically observed in young females by daily hormone administration over a backdrop of GnRH downregulation in order to approximate the FSH and estradiol hormone levels (in the case of AI-HNT) normally observed in each phase of the reproductive cycle in a fertile young female.

Figure 4:
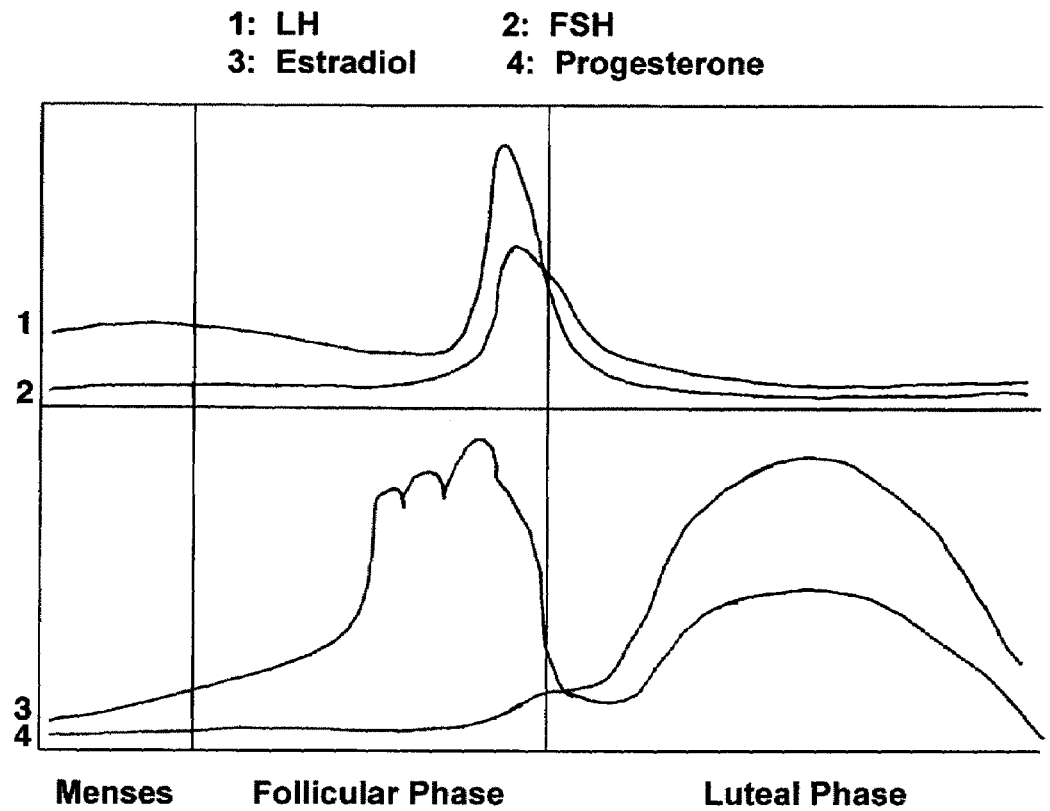
FIG. 4 shows an overview of the durations of hormone administration for the hormones utilized in the Hormone Normalization Therapy (HNT) protocol for treatment Cycles 2 and 3. The X-axis of the graph in the top portion of the figure shows different stages of the menstrual cycle. The Y-axis shows relative levels of FSH, LH, E2 or P4 during a typical menstrual cycle of a young woman. The interval of therapeutic treatment with each of the drugs used in HNT is shown in the bars below the graph. These drugs consist of gonadotropin releasing hormone (GnRH), GnRH agonist, or GnRH antagonist; varying doses of FSH with or without supplementary doses of hCG and/or LH; bolus injection of hCG and/or LH to trigger ovulation; and progesterone as needed for luteal phase support. Aromatase inhibitor HNT (AI-HNT) employs the HNT protocol with the addition of an aromatase inhibitor to the HNT regimen.

A third central concept of hormone normalization therapy is to provide the developing follicle and oocyte with a hormonal milieu that is normal for the entire duration of their maturation. In both mice and humans, the window of hormonal responsiveness of the developing follicle and oocyte is initiated several reproductive cycles before an egg ovulates. In humans, the period of hormonal responsiveness extends at least 50 days (2 menstrual cycles) before ovulation. For this reason, the maturing follicles and oocytes of women with elevated FSH or E2 are subjected to exposure to long-term aberrant hormonal levels for the entire time course of their maturation, leading to errors in chromosome segregation. The hormonal profile in these preceding menstrual cycles as well as in the ovulatory cycle must be normalized to achieve an optimal outcome (maximized fertility, follicular and oocyte quality, and euploid oocyte and conceptus). Normalization using only one or two therapeutic normalization cycles may also have therapeutic value, but three or more therapeutic normalization cycles is preferable. Indeed, oocytes from mice treated with high levels of gonadotropin have an increased incidence of spindle defects, not only within the test cycle, but weeks afterward. In human fertility patients, effects of FSH often spill into the next untreated cycle. FSH receptor mRNA is expressed in a significant fraction of growing primary follicles at least 120 days (4.3 months) prior to ovulation. At least two pre-cycles of hormone normalization therapy are provided to provide time to optimize hormonal dosages to approximate young levels, before the actual treatment cycle, for a total of two full menstrual cycles of treatment plus the follicular phase of the actual test cycle. This will re-establish normal levels of FSH, E2, and other hormones in the body. It is expected that this will significantly increase the success rate of the protocol. The combined protocol of pre-cycles, GnRH/GnRH agonist/GnRH antagonist and FSH treatments during the luteal phases of gonadotropin therapy, and a standardized long treatment duration is a new idea that distinguishes this invention from prior approaches. In addition, the levels of the hormones administered distinguish HNT from other therapies. Drugs used in hormone normalization therapy and in aromatase inhibitor hormone normalization therapy, and the timing of their administration within a single menstrual cycle relative to the reproductive hormonal levels as they occur throughout the cycle are depicted in FIG. 4.

EXAMPLE 3

Therapeutic Regimens

Figure 5:
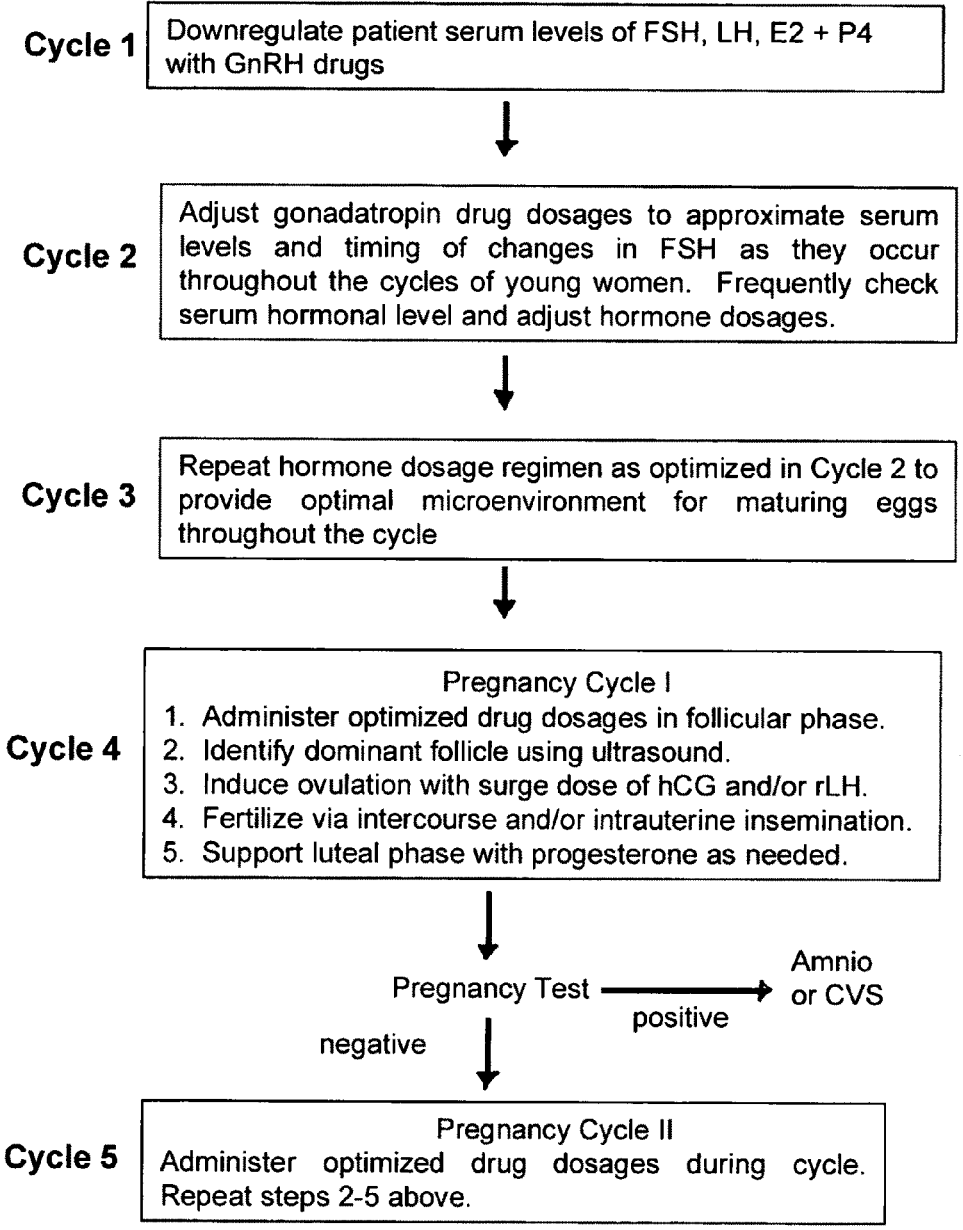
FIG. 5 outlines the clinical protocol for hormone normalization (HNT) therapy for women with high serum FSH. Patients are administered a series of hormonal treatment cycles of four to five menstrual cycles in duration. The regimen of hormonal treatments contains GnRH, GnRH agonist and/or or GnRH antagonist; FSH in doses that vary with the phase of the menstrual cycle with or without hCG and/or LH supplementation; bolus injection of LH and/or hCG to trigger ovulation; and progesterone as needed to provide adequate luteal phase support.

The Hormone Normalization Therapy (HNT) protocol in the clinical trial consists of a control cycle during which gonadotropin and steroid hormone levels are measured prior to treatment (for clinical trial purposes), a downregulation cycle, and a succession of three hormonal treatment cycles, each one menstrual cycle in duration. Patients undergo basal hormone measurements, followed by pituitary downregulation with GnRH, GnRH agonist, or GnRH antagonist, followed by several successive cycles of hormone normalization treatment with low doses of reproductive hormones designed to approximate those of a young woman as they change throughout the menstrual cycle. Patients will then attempt to get pregnant by natural conception or by intrauterine insemination. No IVF is required for these treatments. The basic protocol for hormone normalization therapy is outlined in FIG. 5

The following HNT drug regimen is provided as an outline of how hormone normalization therapy is executed for the aneuploidy study and the pregnancy study, using a drug from each medication class as an example.

General Scheme of Hormonal Treatments and Procedures for the Aneuploidy HNT and AI-HNT Studies The aim of the aneuploidy trial is to compare the incidence of aneuploidy in oocytes from women of advanced maternal age with infertility or previous aneuploid conceptuses before versus after the HNT or AI-HNT therapy.

The HNT and AI-HNT protocols will consist of a downregulation cycle, plus a succession of three hormonal treatment cycles, each one menstrual cycle in duration. In this example, HNT patients will receive treatment with gonadotropin releasing hormone, gonadotropin releasing hormone agonist or antagonist; human menopausal gonadotropin, highly purified human follicle stimulating hormone and/or human recombinant FSH, with or without supplementation with luteinizing hormone activity; and recombinant human LH, recombinant human chorionic gonadotropin, highly purified human chorionic gonadotropin, or urinary human chorionic gonadotropin, to trigger ovulation. Luteal phase progesterone, administered in oil intramuscularly or vaginally as micronized in oil or as a bioadhesive gel, with or without supplementation with orally administered progesterone will be given in cycle 1 as needed, and in the luteal phases of the subsequent cycles if needed for luteal phase support. AI-HNT patients will receive the same drug regimen as HNT patients, with the addition of aromatase inhibitor.

Examples of other drugs that can be used in the protocol are listed in each class as (1) gonadotropin releasing hormone, gonadotropin releasing hormone agonists, and gonadotropin releasing hormone antagonists; (2) follicle stimulating hormone preparations; (3) preparations with luteinizing hormone activity (containing LH and/or hCG); (4) progesterone preparations; (5) aromatase inhibitors. The list of drugs that are used in each class is provided in Table 1. The drugs listed in each class of medications in the example provided here may be substituted with the drugs listed within the same class as in the table, in various permutations and combinations. Dose ranges for these substituted drugs are at the dose ranges that provide comparable bio-activity to the drugs listed in this example.

TABLE ONE

Drugs for use in protocol

| GnRHs and GnRH agonists-for daily or long-acting depot administration | GnRH antagonists |
|---|---|
| Gondaorelin | Abarelix |
| Histrelin | Cetrorelix |
| | Ganirelix |
| | Antarelix |
| | Iturelix (antide) |
| | Nal-glu |
| Nafarelin | orgalutran |
| Leuprolide | |
| Buserelin | |
| Goserelin | |
| Histrelin | |
| Triptorelin | |
| Deslorelin | |
| Fertirelin | |
| FSH drugs | | human urinary menopausal gonadotropin
highly purified follicle stimulating hormone, with or without
human luteinizing hormone or human chorionic gonadotropin
(urinary, highly purified, or recombinant) supplementation
human recombinant follicle stimulating hormone
(follitropin alpha or follitropin beta), with or without an added
supplementary small dose of luteinizing hormone or human chorionic
gonadotropin (urinary, highly purified, or recombinant)
Drugs with luteinizing hormone activity to trigger ovulation human recombinant luteinizing hormone
urinary-derived human chorionic gonadotropin
highly purified human chorionic gonadotropin
human recombinant human chorionic gonadotropin
Progesterone/Progestin progesterone in oil for intramuscular injection
micronized progesterone capsules in oil e.g., prometrium, used as
uteregestan, minagest and microgest for vaginal use; can also be
oral progesterone supplementation
bioadhesive vaginal gels e.g., crinone or prochieve
custom compounded vaginal suppositories
dydrogesterone TABLE ONE-continued Drugs for use in protocol GnRHs and GnRH agonists-for daily or
long-acting depot administration    GnRH antagonists Aromatase inhibitors Letrozole
Exemestane
Anastrozole
Aminogluthemide
Formestane
Vorozole
4-androstene-3,6,17-trione
1,4,6-androstatrien-3,17-dione
testolactone Levels of the gonadotropin and steroid hormones are measured frequently throughout the cycles. Patients will undergo retrieval of oocytes prior to hormonal treatment (in cycle 1), and then after several rounds of hormonal treatment (in cycle 4) will undergo IVF and polar body biopsy, after which biopsied embryos will be transferred back into the uterus.

Cycle 0 (Baseline Hormone Measurement Cycle): Measure levels of FSH, LH, E2, and P4 hormones on a number of days throughout the cycle.

Cycle 1 (Downregulation and Control Retrieval Cycle): Patients will undergo no FSH or GnRH agonist or antagonist treatment in the follicular phase of this cycle. Ovulation induction medication in the form of LH or hCG is administered. Oocytes and surrounding follicular fluid are retrieved from the ovary. The follicular fluid is stored for later hormonal analyses. Copy numbers of chromosomes in the unfertilized oocyte and its polar body (polar body I) are analyzed by comparative genomic hybridization, multicolor fluorescence in situ hybridization, or other methodologies. This provides a control measurement of oocyte aneuploidy prior to HNT. Luteal phase progesterone support is provided in this cycle as needed. Other forms of luteal phase support, including progesterone combined with estradiol, dydrogesterone, or hCG, are also usable as needed to support the luteal phase.

After oocyte retrieval in latter part of Cycle 1, patients are treated with gonadotropin releasing hormone agonist leuprolide to downregulate pituitary secretion of FSH and LH. This permits lowering of follicle stimulating hormone levels that are too high. Leuprolide downregulation is sustained through the follicular and luteal phases of the treatment cycles (during which pregnancy is not attempted), until Cycle 4, wherein the rates of aneuploidy are again measured and pregnancy is attempted. This is done to permit maximum control over FSH levels, which are frequently too high in naturally cycling advanced maternal age women during both the follicular and luteal phases of the cycle; and it normalizes the length of the cycle. Both of these may be detrimental to follicular and oocyte maturation and/or chromosome segregation. These luteal phase treatments are another distinguishing factor of uniqueness of the HNT therapy.

In Cycle 2 (Drug Adjustment Cycle), Leuprolide and FSH drug are administered to approximate the serum levels of FSH and E2 in a fertile 20-25 year old woman on each of the days of the menstrual cycle. For patients with high E2, AI is also administered. Progesterone is administered for luteal phase support as needed. Frequent monitoring of hormonal levels is performed so that doses can be further adjusted to individual differences in patient metabolism of medication.

Cycle 3 (Pre-Cycle), utilizes optimized daily drug dosages established in Cycle 2 to equilibrate AMA patients to a young hormonal milieu throughout the cycle. If significant adjustments are required during Cycle 2 to approximate young hormonal levels, then two rounds of Cycle 3 will be performed before the test cycle (cycle 4) is initiated. Serum hormone levels will continue to undergo regular monitoring in Cycle 3 so that dosages of medication can be adjusted as needed for the individual patient.

In Cycle 4 (Actual Test Cycle), the dosage regimens used in Cycle 3 are utilized with adjustments made in hormonal dosage as-needed, based on continued hormonal measurements. Oocytes and follicular fluid are retrieved from the ovary after the resumption of meiosis is triggered by hCG injection. Intra-follicular hormone levels are quantitated and compared to levels in follicular fluid from Cycle 1. Oocytes then undergo in vitro fertilization with the male partner's sperm. Polar bodies from embryos in the preimplantation stage are then biopsied to remove polar bodies I and II, which are analyzed for chromosome copy number by preimplantation genetic diagnosis (PGD). Embryos after biopsy are transferred back into the uterus. Luteal phase progesterone support is provided and the patient is given a pregnancy test approximately 15 days after retrieval. Pregnancies are followed for evidence of clinical progression and viability.

In Cycle 5 (IUI Pregnancy cycle), the patients who do not get pregnant in Cycle 4 are asked to perform another HNT cycle to attempt pregnancy in Cycle 5 (an IUI HNT test cycle). HNT hormones are administered in this cycle as have been in cycles 3 and 4. Patients who go through this cycle undergo intrauterine insemination (IUI) with male partner's serum rather than IVF. Pregnancy test is administered on these patients approximately 15 days after IUI. Pregnant patients are followed for evidence of clinical progression and viability and those who do not get pregnant are offered the option of attempting pregnancy in another cycle (Cycle 6) with the same protocol as Cycle 5. A single pregnancy attempt in the HNT protocol takes about 2 months longer than a typical IVF or egg donation cycle.

Specific Therapeutic Regimens

The protocol provided is a specific example to teach the art of the HNT therapy. The therapy may also be performed using doses of the other medications listed in Table 1 that give a comparable range of bio-activity for that class of medication. Brown was first to report that threshold levels of FSH in the body are needed to stimulate follicular development to ovulation (Brown, J B. Aust N Z J Obstet. Gynecol. 18: 47-54, 1978). Below these FSH levels, follicular development does not occur. There is inter-patient variability in the dosage of FSH that is required to achieve follicular development, likely due to patient differences in FSH metabolic clearance rates and distribution volumes (Schoemaker, J, et al. Bailliere's Clinical Obstetrics and Gynecology 7: 297-308, 1993). Studies by van Weissenbruch and by Schoemaker et al. found that despite this variability in required FSH dosages required to induce follicular development to ovulation, a uniform threshold level of serum FSH was necessary and sufficient for follicular growth to ovulation (in the Schoemaker study, the FSH threshold was 7.8 IU but this may vary somewhat with the method of FSH quantitation used by a given clinic). This threshold level is within the normal range of quantitative values for FSH in the early follicular phase for a young and fertile woman (ibid and references therein).

In performing FSH administration during HNT, a successful treatment regimen will be one in which sufficient FSH is supplied to permit follicular development, while at the same time providing low enough FSH dosages to approximate the range of serum FSH levels that are observed in a fertile young woman. The protocol provided below is an example designed to provide a means to achieve dosages that meet both these criteria.

Specific Therapy with Specific Drugs.

The protocol provided is a specific example to teach the art of the HNT therapy. The therapy may also be performed using doses of the other medications listed in Table 1 that give a comparable range of bio-activity for that class of medication.

Cycle 1 (Downregulation and Control Retrieval Cycle)

1. Monitor FSH and LH, P4, and E2 levels by frequent serum measurements throughout the cycle.
2. Monitor progression of follicular growth when patient is in mid-cycle (day 7 and onward) by performing frequent successive transvaginal ultrasounds to closely monitor follicular development until the dominant follicle reaches 18-19 mm. A single follicle is expected since this is a natural ovulatory cycle.
3. Trigger ovulation by subcutaneous injection of 10,000 international units of highly purified hCG (Pregnyl). Patients will be asked not to attempt pregnancy. Intercourse to achieve pregnancy will not be attempted.
4. 36 hours later, perform transvaginal ultrasound-guided oocyte aspiration under light intravenous sedation. Oocytes and the surrounding follicular fluid will be retrieved from the patient at this time. Fertilization will not be attempted.
5. Place oocytes in fixative and perform comparative genomic hybridization analysis, multi-color fluorescence in-situ hybridization, or other methodologies suited to assess chromosome copy number.
6. Perform quantitative analyses of FSH and E2 levels assayed in follicular fluid. Quantitation of other molecules can also be performed.
7. Provide luteal phase support with 200 mg prometrium (progesterone) capsules, BID administered daily and vaginally to permit sufficiently high levels of luteal phase uterine progesterone, as needed.
8. On day 21 of the cycle, initiate administration of leuprolide, 1 mg/day subcutaneous injection until the beginning of the Cycle 2. Alternatively, patients may be provided with an intramuscular long-acting depot injection of lupron (Depot Lupron), such as monthly injections of month long acting depot lupron (7.5 mg/month depot lupron injected intramuscularly (IM), a single three-month lupron injection (22.5 mg/3 months IM), a single four month lupron injection (30 mg/4 months IM), or a combination thereof.
9. Patients receiving prometrium will terminate it several days before expected menses to trigger menstruation.

Cycle 2 (Drug Adjustment Cycle).

1. Assess downregulation 10-14 days after the first leuprolide dose by vaginal ultrasound and measurement of serum estradiol and FSH.
2. Continue frequent measurements of patient's FSH and E2 levels throughout Cycle 2.
3. Day 1 of cycle 2 is defined as the day on which FSH injections are started (see below for protocol). On Day 1 of cycle 2, reduce dose of leuprolide from 1 mg/day as given in cycle 1, down to 0.5 mg/day (subQ). 0.5 mg/day leuprolide administration will continue uninterrupted throughout the entirety of cycles 2 and 3, and until shortly prior to the time of retrieval in cycle 4.
4. Start FSH treatments. FSH will be human menopausal gonadotropin, or will be recombinant human FSH (rFSH, follitropin alpha) or highly purified FSH, with or without prescription of daily supplementary LH activity medication (e.g., hCG).

The FSH treatment regimen in this protocol is designed to approximate the levels of FSH in the young female throughout the cycle. To accomplish this, Cycle 2, unlike the other HNT treatment cycles, is comprised of two phases. Phase I is designed to identify the minimal dose of FSH required for the patient to achieve threshold levels of FSH conducive to follicular development. Phase II of cycle 2, and Cycles 3 and 4, are designed to approximate normal FSH levels throughout the menstrual cycles in the patient. This protocol design will minimize the likelihood of administering dosages of FSH that may lead to levels of FSH that fall above or below the range of normal FSH levels for a young and fertile woman.

Phase I of Cycle 2: Finding a Threshold Dosage of FSH for Each Patient

The first day of FSH injection is defined as Day 1 of Cycle 2. Patients will administer subQ injections of FSH in a ramp-up fashion in the early phase of cycle 2, followed by a ramp-down phase of the protocol later in cycle 2. This will be with or without subQ co-administration of 10 international units of supplementary hCG (total 10 IU per day; Pregnyl). Patients will continue daily injections of GnRH agonist for the duration of the follicular and luteal phases of the cycle, and will perform the following schedule for injections of FSH:

Day 1: Patients will receive 50 IU/day sc of FSH starting on day one of FSH treatment (25 IU AM and PM). Patients will be treated in this way for 4 days.

Day 5: Patients will undergo serum quantitation of FSH levels. FSH quantitation will be performed on day 5 because it takes 4 days for steady-state levels of FSH to be established in a woman being given daily FSH injections at a given dosage. If FSH level does not meet or exceed the threshold FSH level, the dosage of FSH will be increased to 75 IU/day (37.5 IU AM and PM) for 4 days.

Day 9: Quantitate serum FSH levels. If FSH level does not meet or exceed the threshold FSH level, the dosage of FSH will be increased to 100 IU rFSH/day (50 IU AM and PM) for 4 days.

Day 13: Quantitate serum FSH levels. If FSH level does not meet or exceed the threshold FSH level, the dosage of FSH will be increased to 150 IU rFSH/day (75 IU AM and PM) for 4 days.

Day 17: Quantitate serum FSH levels. If FSH level does not meet or exceed the threshold FSH level, the dosage of FSH will be increased to 200 IU rFSH/day (100 IU AM and PM) for 4 days.

This pattern will be continued as needed in FSH increments until the serum FSH threshold level is met for that specific patient.

Phase II of Cycle 2. Hormone Normalization Starting with the Threshold Dosage and Proceeding Through the Cycle Once the serum FSH threshold level is reached, the daily dosage will be decreased in several phases to emulate the normal hormonal changes across the cycle that occur in a young woman. For instance, take the example of a patient who reaches the threshold FSH level at daily FSH dosage of 100 IU/day as measured on day 13. For a patient who responds in this manner, the ramping up of dosages would stop on this day, and the protocol would then proceed as explained below.

Days 13-15: 75 IU rFSH/day (37.5 IU FSH 2×/day, subQ, AM and PM), with or without daily hCG supplementation (10 IU total).

Days 16-18: 50 IU rFSH/day (25 IU FSH 2×/day, subQ, AM and PM), with or without daily hCG supplementation (10 IU total).

Day 19 (this is an approximation; exact day occurs when follicle reaches approximately 18 mm): 150 IU rFSH+10,000

IU of hCG (75 IU FSH subQ in PM; +10,000 IU highly purified hCG (Pregnyl) PM shot timed to be 36 hours prior to scheduled retrieval time). Daily administration of FSH doses may be extended until the mature follicle is detected.

Days 20-30: no FSH

Days 31 to day 1 of NEXT cycle (i.e., first day of menses): 50 IU rFSH (25 IU FSH 2×/day, subQ, AM and PM)

Day 2 of NEXT CYCLE (Cycle 3): 100 IU (50 IU FSH/day 2×/day, subQ, AM and PM).

Patients who achieve threshold serum levels of FSH at 50 IU, 75 IU, 150 IU, 200 IU or other daily FSH dosages during Phase I of Cycle 2 will receive a ramped-down regimen of rFSH dosages during Phase II of Cycle 2 that is analogous to the one described above. These patients may also receive daily dosage of hCG (10 IU) and luteal phase prometrium support (200 mg BID) as the patients with who reach the FSH threshold at a dose of 150 IU FSH.

Patients are given ultrasound evaluations starting 6 days after their first FSH injection, and will be prescribed estradiol, FSH measurements, and additional ultrasounds every several days thereafter. This will permit the physician to monitor for a normal rate of follicular growth (1-2 mm/day), count the number of growing follicles, and provide individual adjustments in medication dosages to accommodate patient metabolism of medication. Ultrasound measurements will also permit determination of when a follicle is mature (18 mm or more). Administration of FSH may be extended beyond day 18, until the mature follicle is detected, whereupon the 150 IU rFSH+10,000 IU hCG injection will be administered. In a modification of this protocol, rFSH injections are supplemented daily throughout the menstrual cycle with 37.5 amp of rLH (Luveris) 2× per day (subQ injection). Prometrium capsules, vaginally administered 200 mg BID, are added to the luteal phases of cycles 2, 3, and 4 if needed, as determined by luteal phase measurements in a previous cycle.

Cycle 3: Pre-cycle

Tests for serum hormones are performed at regular intervals throughout this cycle (as well as the subsequent cycles), and administration of leuprolide, rFSH, hCG, and letrozole (for AI-HNT patients) are performed as described for Cycle 2, with adjustments made based on these serum measurements in order to accommodate individual patient metabolism of drugs, as described above to approximate young hormonal levels. The longer ramp-up testing phase that was performed in Phase I of cycle 2 to determine FSH dosage required to achieve threshold levels need not be repeated in Cycle 3 or Cycle 4. By way of example the following protocol would be given, assuming that 100 IU FSH/day was the initial dose that had been found to achieve threshold serum FSH levels conducive to follicular development:

Days 2-4: 100 IU rFSH (50 IU, 2×/day, subQ, AM and PM), with or without daily hCG supplementation (10 IU/day).

Days 5-7: 75 IU rFSH (37.5 IU FSH/day, 2×/day, subQ, AM and PM), with or without daily hCG supplementation (10 IU/day).

Days 8-14: 50 IU rFSH (25 IU FSH/day, 2×/day, subQ, AM and PM), with or without daily hCG supplementation (10 IU).

Day 14 (exact day occurs when follicle reaches approximately 18 mm): 150 IU rFSH+10,000 units of hCG (Pregnyl) shot timed to be approximately 36 hours prior to scheduled retrieval time)

Days 15-25: no FSH

Days 26-day 1 of NEXT cycle: 50 IU rFSH/day (25 IU FSH, 2×/day, subQ, AM and PM)

Day 2 of NEXT CYCLE: 100 IU rFSH (75 IU rFSH, 2×/day, subQ, AM and PM)—then proceed exactly the same way in the subsequent cycles as described above, with adjustments in individual dosages as needed to accommodate patient metabolism of medications.

Cycle 4: The Test Cycle

1. Hormone tests, and administration of leuprolide, FSH, and letrozole (for AI-HNT patients) will be performed throughout the follicular phase as described in Cycle 3, with adjustments made to accommodate individual patient metabolism of drugs as described above to approximate young hormonal levels.

2. Monitor progression of follicular growth when patient is in mid-cycle by performing ultrasounds in mid-follicular phase starting day 7 of the cycle. Perform ultrasounds frequently beginning in the mid-follicular phase until the dominant follicle reaches 18-19 mm. A single follicle is usually expected since hormonal levels and their timing within an HNT cycle are designed to approximate those that occur in a natural cycle, during which single follicles are generally obtained.

3. Induce ovulation by subcutaneous injection of 10,000 international units of highly purified hCG (Pregnyl). Pregnancy will not be attempted.

4. 36 hours later, perform transvaginal ultrasound-guided oocyte aspiration under light intravenous sedation to retrieve the oocyte from each patient. Oocytes and the surrounding follicular fluid will be retrieved at this time. In vitro fertilization will be performed. Oocytes will undergo in vitro fertilization with the male partner's sperm. Polar bodies from embryos grown in the laboratory to the pre-implantation stage are then biopsied to remove polar bodies I and II, which are analyzed for chromosome copy number by preimplantation genetic diagnosis (PGD). Embryos after biopsy are transferred back into the uterus. Luteal phase progesterone support is provided (200 mg prometrium BID daily vaginal administration). rFSH at a dosage of 37.5 IU 2×/day (AM and PM) will be given starting on day 26 until day 28, whereupon a pregnancy test will be administered. Patients will be given a pregnancy test approximately 15 days after retrieval. Patients with a positive pregnancy test are followed for evidence of clinical progression and viability of the pregnancy, according to standard of care for OB/Gyn patients in early pregnancy.

Cycle 5: Pregnancy Test Cycle

Patients who do not get pregnant in Cycle 4 will be provided an opportunity attempt pregnancy in a fifth cycle, This can be regarded as a good opportunity by the patient since their hormonal levels will have been optimized in the course of the several months of therapy, Hormone administration will be performed as described in Cycle 4 using optimized dosages and regular serum hormone and ultrasound monitoring. This hormonal treatment will be started as described for Day 1 of the HNT therapy. Administration of hCG to trigger ovulation will be performed as proscribed in cycle 4 once follicles mature to 18-19 mm. Luteal phase progesterone support is provided (200 mg prometrium BID daily vaginal administration). rFSH at a dosage of 37.5 IU 2×/day (AM and PM) will be given starting on day 26 until day 28, whereupon a pregnancy test will be administered. Patients with a positive pregnancy test are followed for evidence of clinical progression and viability of the pregnancy, according to standard of care for OB/Gyn patients in early pregnancy.

EXAMPLE 4

General Scheme of Hormonal Treatments and Procedures for Pregnancy Studies Using HNT and AI-HNT The aim of the pregnancy trial is to quantitate pregnancy success rates for female patients of advanced maternal age with previous miscarriages or infertility after the HNT or AI-HNT therapy, and compare it to the pregnancy rates achieved by conventional controlled ovarian hyperstimulation (COHS) therapy. Pregnancy success for miscarriage patients will be defined as the percentage of successful pregnancies (defined as clinical pregnancies with normal karyotype). Pregnancy success for infertile patients will be defined as the rate of pregnancies. The HNT and AI-HNT protocols will consist of a downregulation cycle, plus a succession of three hormonal treatment cycles, each one menstrual cycle in duration. In this example, as for the aneuploidy trial, HNT patients will receive treatment with gonadotropin releasing hormone, gonadotropin releasing hormone agonist, or gonadotropin releasing hormone antagonist. As for HNT, in Phase I of Cycle 2 they will undergo a dose-response period to optimize dosages to achieve target levels of serum FSH. This, and the ensuing treatment phase that occurs in Phase II of cycle 2 will be performed using human menopausal gonadotropin, highly purified human follicle stimulating hormone or human recombinant, FSH, with or without supplementation with recombinant human LH, recombinant human chorionic gonadotropin, highly purified human chorionic gonadotropin, or urinary human chorionic gonadotropin. Ovulation is triggered with a bolus injection of hCG or LH. Luteal phase progesterone, administered in oil IM or vaginally as micronized in oil or as a bioadhesive gel, and with or without supplementation with orally administered progesterone, will be given on an as-needed basis. AI-HNT patients will receive the same drug regimen as HNT patients, with the addition of aromatase inhibitor. Patients will attempt pregnancy by timed intercourse with male partner and/or intrauterine insemination with male partner's sperm.

Examples of drugs that can be used in the protocol are listed in each class as listed above in Table 1. The drugs listed in the example provided here may be substituted with the drugs listed within their respective drug classes in the table, in various permutations and combinations. Dose ranges for these substituted drugs within each drug class are at the dose ranges that provide comparable bio-activity to the drugs listed in this example. Levels of gonadotropin and steroid hormones will be measured frequently throughout the cycles.

Cycle 1: Downregulation Cycle

Patients will undergo no FSH or GnRH agonist or antagonist treatment in the follicular phase of the cycle. Patients will undergo downregulation with leuprolide starting in the mid-luteal phase of the cycle.

In Cycle 2 (Drug Adjustment Cycle) Leuprolide will be continued throughout the cycle. In Phase I of Cycle 2 dosages of FSH that yield FSH levels that approximate threshold levels will be determined as described for HNT above. In this way, doses of FSH, and in the case of AI-HNT patients, aromatase inhibitors, are administered that would be expected to approximate serum levels of FSH for a fertile 20-25 year old woman as they vary throughout the menstrual cycle. Dosages of aromatase inhibitors will also be administered for women with elevated E2 in order to approximate young E2 serum levels, according to the protocol described below for AI patients. Frequent monitoring of hormonal levels will be performed so that doses can be further adjusted to individual differences in patient metabolism of medication.

In Cycle 3 (Pre-Cycle) we will utilize optimized daily drug dosages established in Cycle 2 to equilibrate AMA patients to a young hormonal milieu throughout the cycle. Aromatase inhibitors will be provided for AI patients during this cycle.

In Cycle 4 (Actual Pregnancy Cycle) we will again provide the dosage regimens used in Cycle 3 throughout the follicular phase of the cycle. Aromatase inhibitors will be provided for AI patients during this cycle. Ovulation will be triggered by hCG and/or LH injection and patients will be inseminated with male partner's sperm. A pregnancy test will be administered 15 days after insemination (IUI). If the pregnancy test is positive the pregnancy will be followed for clinical viability.

Cycle 5. If the pregnancy test is negative, a fifth cycle of hormonal treatments will be offered to the patient.

Specific Example of the Therapy with Specific Drugs

The protocol provided is a specific example to teach the art of the HNT therapy. The therapy may also be performed using doses of the other medications listed in Table 1, using doses that give a comparable range of bio-activity for that class of medication, as judged by one skilled in the art.

Cycle 1: Downregulation Cycle

1. Monitor FSH and estradiol levels by frequent serum measurements.
2. On day 21 of the cycle, initiate administration of leuprolide, 1 mg/day subcutaneous injection until the beginning of the Cycle 2.
3. Assess downregulation 10-14 days after the first leuprolide dose by vaginal ultrasound and measurement of serum estradiol and FSH.

Cycle 2: Drug Adjustment Cycle

1. Assess downregulation 10-14 days after the first leuprolide dose by vaginal ultrasound and measurement of serum estradiol and FSH.
2. Continue frequent measurements of patient's FSH and E2 levels throughout Cycle 2.
3. Day 1 of cycle 2 is defined as the day on which FSH injections are started (see below for protocol). On Day 1 of cycle 2, reduce dose of leuprolide from 1 mg/day as given in cycle 1, down to 0.5 mg/day (subQ). 0.5 mg/day leuprolide administration will continue uninterrupted throughout the entirety of cycles 2 and 3, and until shortly prior to the time of retrieval in cycle 4.
4. Start FSH treatments. FSH will be human menopausal gonadotropin, or will be recombinant human FSH (rFSH, follitropin alpha) or highly purified FSH, with or without prescription of daily supplementary LH activity medication (e.g., hCG).

The FSH treatment regimen in this protocol is designed to approximate the levels of FSH in the young female throughout the cycle. To accomplish this, Cycle 2, unlike the other HNT treatment cycles, is comprised of two phases. Phase I is designed to identify the minimal dose of FSH required for the patient to achieve threshold levels of FSH conducive to follicular development. Phase II of cycle 2, and Cycles 3 and 4, are designed to approximate normal FSH levels throughout the menstrual cycles in the patient. This protocol design will minimize the likelihood of administering dosages of FSH that may lead to levels of FSH that fall above or below the range of normal FSH levels for a young and fertile woman.

Phase I of Cycle 2: Finding a Threshold Dosage of FSH for Each Patient

The first day of FSH injection is defined as Day 1 of Cycle 2. Patients will administer subQ injections of FSH in a ramp-up fashion in the early phase of cycle 2, followed by a ramp-down phase of the protocol later in cycle 2. This will be with or without subQ co-administration of 10 international units of supplementary hCG (total 10 IU per day; Pregnyl). Patients will continue daily injections of GnRH agonist for the duration of the follicular and luteal phases of the cycle, and will perform the following schedule for injections of FSH:

Day 1: Patients will receive 50 IU/day sc of FSH starting on day one of FSH treatment (25 IU AM and PM). Patients will be treated in this way for 4 days.

Day 5: Patients will undergo serum quantitation of FSH levels. FSH quantitation will be performed on day 5 because it takes 4 days for steady-state levels of FSH to be established in a woman being given daily FSH injections at a given dosage. If FSH level does not meet or exceed the threshold FSH level, the dosage of FSH will be increased to 75 IU/day (37.5 IU AM and PM) for 4 days.

Day 9: Quantitate serum FSH levels. If FSH level does not meet or exceed the threshold FSH level, the dosage of FSH will be increased to 100 IU rFSH/day (50 IU AM and PM) for 4 days.

Day 13: Quantitate serum FSH levels. If FSH level does not meet or exceed the threshold FSH level, the dosage of FSH will be increased to 150 IU rFSH/day (75 IU AM and PM) for 4 days.

Day 17: Quantitate serum FSH levels. If FSH level does not meet or exceed the threshold FSH level, the dosage of FSH will be increased to 200 IU rFSH/day (100 IU AM and PM) for 4 days.

This pattern will be continued as needed in FSH increments until the serum FSH threshold level is met for that specific patient.

Phase II of Cycle 2. Hormone Normalization Starting with the Threshold Dosage and Proceeding Through the Cycle Once the serum FSH threshold level is reached, the daily dosage will be decreased in several phases to emulate the normal hormonal changes across the cycle that occur in a young woman. For instance, take the example of a patient who reaches the threshold FSH level at daily FSH dosage of 100 IU/day as measured on day 13. For a patient who responds in this manner, the ramping up of dosages would stop on this day, and the protocol would then proceed as explained below.

Days 13-15: 75 IU rFSH/day (37.5 IU FSH 2×/day, subQ, AM and PM), with or without daily hCG supplementation (10 IU total).

Days 16-18: 50 IU rFSH/day (25 IU FSH 2×/day, subQ, AM and PM), with or without daily hCG supplementation (10 IU total).

Day 19 (this is an approximation; exact day occurs when follicle reaches approximately 18 mm): 150 IU rFSH+10,000 IU of hCG (75 IU FSH subQ in PM; +10,000 IU highly purified hCG (Pregnyl) PM shot timed to be 36 hours prior to scheduled retrieval time). Daily administration of FSH doses may be extended until the mature follicle is detected.

Days 20-30: no FSH

Days 31 to day 1 of NEXT cycle (i.e., first day of menses): 50 IU rFSH (25 IU FSH 2×/day, subQ, AM and PM)

Day 2 of NEXT CYCLE (Cycle 3): 100 IU (50 IU FSH/day 2×/day, subQ, AM and PM).

Patients who achieve threshold serum levels of FSH at 50 IU, 75 IU, 150 IU, 200 IU or other daily FSH dosages during Phase I of Cycle 2 will receive a ramped-down regimen of rFSH dosages during Phase II of Cycle 2 that is analogous to the one described above. These patients may also receive daily dosage of hCG (10 IU) and luteal phase prometrium support (200 mg BID) as the patients with who reach the FSH threshold at a dose of 150 IU FSH.

Patients are given ultrasound evaluations starting 6 days after their first FSH injection, and will be prescribed estradiol, FSH measurements, and additional ultrasounds every several days thereafter. This will permit the physician to monitor for a normal rate of follicular growth (1-2 mm/day), count the number of growing follicles, and provide individual adjustments in medication dosages to accommodate patient metabolism of medication. Ultrasound measurements will also permit determination of when a follicle is mature (18 mm or more). Administration of FSH may be extended beyond day 18, until the mature follicle is detected, whereupon the 150 IU rFSH+10,000 IU hCG injection will be administered. In a modification of this protocol, rFSH injections are supplemented daily throughout the menstrual cycle with 37.5 amp of rLH (Luveris) 2× per day (subQ injection). Prometrium capsules, vaginally administered 200 mg BID, are added to the luteal phases of cycles 2, 3, and 4 if needed, as determined by luteal phase measurements in a previous cycle.

Cycle 3: Pre-cycle

Tests for serum hormones are performed at regular intervals throughout this cycle (as well as the subsequent cycles), and administration of leuprolide, rFSH, hCG, and letrozole (for AI-HNT patients) are performed as described for Cycle 2, with adjustments made based on these serum measurements in order to accommodate individual patient metabolism of drugs, as described above to approximate young hormonal levels. The longer ramp-up testing phase that was performed in Phase I of cycle 2 to determine FSH dosage required to achieve threshold levels need not be repeated in Cycle 3 or Cycle 4. By way of example the following protocol would be given, assuming that 100 IU FSH/day was the initial dose that had been found to achieve threshold serum FSH levels conducive to follicular development:

Days 2-4: 100 IU rFSH (50 IU, 2×/day, subQ, AM and PM), with or without daily hCG supplementation (10 IU/day).

Days 5-7: 75 IU rFSH (37.5 IU FSH/day, 2×/day, subQ, AM and PM), with or without daily hCG supplementation (10 IU/day).

Days 8-14: 50 IU rFSH (25 IU FSH/day, 2×/day, subQ, AM and PM), with or without daily hCG supplementation (10 IU).

Day 14 (exact day occurs when follicle reaches approximately 18 mm): 150 IU rFSH+10,000 units of hCG (Pregnyl) shot timed to be approximately 36 hours prior to scheduled retrieval time)

Days 15-25: no FSH

Days 26-day 1 of NEXT cycle: 50 IU rFSH/day (25 IU FSH, 2×/day, subQ, AM and PM)

Day 2 of NEXT CYCLE: 100 IU rFSH (75 IU rFSH, 2×/day, subQ, AM and PM)—then proceed exactly the same way in the subsequent cycles as described above, with adjustments in individual dosages as needed to accommodate patient metabolism of medications.

Cycle 4: The Test Cycle

1. Hormone tests, and administration of leuprolide, FSH, and letrozole (for AI-HNT patients) will be performed throughout the follicular phase as described in Cycle 3, with adjustments made to accommodate individual patient metabolism of drugs as described above to approximate young hormonal levels.

2. Monitor progression of follicular growth when patient is in mid-cycle by performing ultrasounds in mid-follicular phase starting day 7 of the cycle. Perform ultrasounds frequently beginning in the mid-follicular phase until the dominant follicle reaches 18-19 mm. A single follicle is usually expected since hormonal levels and their timing within an HNT cycle are designed to approximate those that occur in a natural cycle, during which single follicles are generally obtained.

3. Induce ovulation by subcutaneous injection of 10,000 international units of highly purified hCG (Pregnyl).
4. Approximately 32-38 hours later, perform intrauterine insemination with partner's sperm. Luteal phase progesterone support is provided as needed with prometrium 200 mg daily BID.
5. Resume rFSH treatments at a dose of 37.5 IU 2×/day (AM and PM) sc starting day 26. Patient is given a pregnancy test approximately 15 days after intrauterine insemination. Patients with a positive pregnancy test are followed for evidence of clinical progression and viability of the pregnancy, according to standard of care for OB/Gyn patients in early pregnancy.

Cycle 5: Pregnancy Test Cycle

Patients who do not get pregnant in Cycle 4 will be provided an opportunity attempt pregnancy in a fifth cycle, Hormone administration will be performed as described in cycle 4 using optimized dosages and regular serum hormone and ultrasound monitoring. This hormonal treatment will be started as described for Day 1 of the HNT therapy. Administration of hCG to trigger ovulation will be performed as proscribed in cycle 4 once follicles mature to 18-19 mm. Luteal phase progesterone support is provided as needed (200 mg prometrium BID daily vaginal administration). Patients will be given a pregnancy test approximately 15 days after intrauterine insemination. Patients with a positive pregnancy test are followed for evidence of clinical progression and viability of the pregnancy, according to standard of care for OB/Gyn patients in early pregnancy.

EXAMPLE 5

Strategy of AI-Hormone Normalization Therapy

Like hormone normalization therapy, a fundamental objective of aromatase inhibitor-hormone normalization therapy is to restore young hormonal levels to advanced maternal age women in order to guide follicular and oocyte development to promote correct chromosomal segregation. The procedure for aromatase inhibitor-hormone normalization therapy is similar to that of hormone normalization therapy (Compare FIGS. 5 and 6).

As in hormone normalization therapy, pituitary function is controlled by administration of GnRH agonist or antagonist, and young levels of FSH are reconstituted by administration of exogenous follicle stimulating hormone. Also, as in hormone normalization therapy, progesterone is added back as needed to permit normal luteal phase support. The improvement that is provided by the aromatase inhibitor-hormone normalization therapy is that the addition of aromatase inhibitor allows one to directly control estradiol production. This is a significant improvement because the hormone normalization therapy protocol only permits indirect control of estradiol levels via its downregulation of FSH secretion. However, data in the literature indicate the existence of a class of patients, typically of advanced maternal age, who produce excessive estradiol that may not be controlled by suppressing excessive FSH secretion. Thus the hormone normalization therapy protocol is supplemented with low dose aromatase inhibitor treatment during the hormone normalization therapy regimen to normalize estradiol to approximate the levels typically observed in a fertile woman in her 20s.

Specific HNT and AI Drugs in Aneuploidy Trial.

The protocol provided is a specific example to teach the art of the AI-HNT therapy. The therapy may also be performed using doses of the other medications listed in Table 1 that give a comparable range of bio-activity for that class of medication.

Cycle 1: Downregulation and Control Retrieval Cycle
1. Monitor FSH and LH, P4, and E2 levels by frequent serum measurements throughout the cycle.
2. Monitor progression of follicular growth when patient is in mid-cycle (day 7 and onward) by performing frequent successive transvaginal ultrasounds to closely monitor follicular development until the dominant follicle reaches 18-19 mm. A single follicle is expected since this is a natural ovulatory cycle.
3. Trigger ovulation by subcutaneous injection of 10,000 international units of highly purified hCG (Pregnyl). Patients will be asked not to attempt pregnancy. Intercourse to achieve pregnancy will not be attempted.
4. 36 hours later, perform transvaginal ultrasound-guided oocyte aspiration under light intravenous sedation. Oocytes and the surrounding follicular fluid will be retrieved from the patient at this time. Fertilization will not be attempted.
5. Place oocytes in fixative and perform comparative genomic hybridization analysis, multi-color fluorescence in-situ hybridization, or other method to assess chromosome copy number.
6. Perform quantitative analyses of FSH and E2 levels assayed in follicular fluid. Quantitation of other molecules can also be performed.
7. Provide luteal phase support with 200 mg prometrium (progesterone) capsules, BID administered daily and vaginally to permit sufficiently high levels of luteal phase uterine progesterone, as needed.
8. On day 21 of the cycle, initiate administration of leuprolide, 1 mg/day subcutaneous injection until the beginning of the Cycle 2.
9. Patients receiving prometrium treatments will terminate it several days before expected menses to trigger menstruation.

Cycle 2: Drug Adjustment Cycle
1. Assess downregulation 10-14 days after the first leuprolide dose by vaginal ultrasound and measurement of serum estradiol and FSH.
2. Continue frequent measurements of patient's FSH and E2 levels throughout Cycle 2.
3. Day 1 of cycle 2 is defined as the day on which FSH injections are started (see below for protocol). On Day 1 of cycle 2, reduce dose of leuprolide from 1 mg/day as given in cycle 1, down to 0.5 mg/day (subQ). 0.5 mg/day leuprolide administration will continue uninterrupted throughout the entirety of cycles 2 and 3, and until shortly prior to the time of retrieval in cycle 4.
4. Start FSH treatments. FSH will be human menopausal gonadotropin, or will be recombinant human FSH (rFSH, follitropin alpha) or highly purified FSH, with or without prescription of daily supplementary LH activity medication (e.g., hCG).

The FSH treatment regimen in this protocol is designed to approximate the levels of FSH in the young female throughout the cycle. To accomplish this, Cycle 2, unlike Cycles 3 and 4, is comprised of two phases. Phase I is designed to identify the minimal dose of FSH required for the patient to achieve threshold levels of FSH conducive to follicular development. For AI HNT patients, Phase I of cycle 2 will also serve as the initial optimization phase for administration of AI medication to achieve young E2 levels. Phase II of cycle 2, and Cycles 3 and 4, are designed to approximate normal FSH and E2 levels throughout the menstrual cycles in the patient with high estradiol and normal or high FSH. This protocol design will diminish the likelihood of administering dosages of FSH and AI that may lead to levels of FSH and E2 that fall above or below the ranges of normal FSH and E2 that are found in a young and fertile woman.

Phase I of Cycle 2: Finding a Threshold/Young Normal Level of FSH and a Normal Level of E2 for Each Patient During FSH and AI Administration The first day of FSH injection is defined as Day 1 of Cycle 2. Patients will administer subQ injections of FSH in a ramp-up fashion in the early phase of cycle 2, followed by a ramp-down phase of the protocol later in cycle 2. This will be with or without subQ co-administration of 10 international units of supplementary hCG (total 10 IU per day; Pregnyl). Patients will continue daily injections of GnRH agonist for the duration of the follicular and luteal phases of the cycle, and will perform the following schedule for injections of FSH:

Day 1: Patients will receive 50 IU/day sc of FSH starting on day one of FSH treatment (25 IU AM and PM). Patients will be treated in this way for 4 days.

Day 5: Patients will undergo serum quantitation of FSH levels. FSH quantitation will be performed on day 5 because it takes 4 days for steady-state levels of FSH to be established in a woman being given daily FSH injections at a given dosage. If FSH level does not meet or exceed the threshold FSH level, the dosage of FSH will be increased to 75 IU/day (37.5 IU AM and PM) for 4 days.

Day 9: Quantitate serum FSH levels. If FSH level does not meet or exceed the threshold FSH level, the dosage of FSH will be increased to 100 IU rFSH/day (50 IU AM and PM) for 4 days.

Day 13: Quantitate serum FSH levels. If FSH level does not meet or exceed the threshold FSH level, the dosage of FSH will be increased to 150 IU rFSH/day (75 IU AM and PM) for 4 days.

Day 17: Quantitate serum FSH levels. If FSH level does not meet or exceed the threshold FSH level, the dosage of FSH will be increased to 200 IU rFSH/day (100 IU AM and PM) for 4 days.

This pattern will be continued as needed in FSH increments until the serum FSH threshold level is met for that specific patient. For a summary of the protocol see FIG. 6.

Phase II of Cycle 2: Hormone Normalization Starting with the Threshold Dosage and Proceeding Through the Cycle for AI Patients Once the serum FSH threshold level is reached, the daily dosage will be decreased in several phases to emulate the normal hormonal changes across the cycle that occur in a young woman. For instance, take the example of a patient who reaches the threshold FSH level at daily FSH dosage of 100 IU/day as measured on day 13. For a patient who responds in this manner, the ramping up of dosages would stop on this day, and the protocol would then proceed as explained below.

Days 13-15: 75 IU rFSH/day (37.5 IU FSH 2×/day, subQ, AM and PM), with or without daily hCG supplementation (10 IU total).

Days 16-18: 50 IU rFSH/day (25 IU FSH 2×/day, subQ, AM and PM), with or without daily hCG supplementation (10 IU total).

Day 19 (this is an approximation; exact day occurs when follicle reaches approximately 18 mm): 150 IU rFSH+10,000 IU of hCG (75 IU FSH subQ in PM; +10,000 IU highly purified hCG (Pregnyl) PM shot timed to be 36 hours prior to scheduled retrieval time). Daily administration of FSH doses may be extended until the mature follicle is detected.

Days 20-30: no FSH

Days 31 to day 1 of NEXT cycle (i.e., first day of menses): 50 IU rFSH (25 IU FSH 2×/day, subQ, AM and PM)

Day 2 of NEXT CYCLE (Cycle 3): 100 IU (50 IU FSH/day 2×/day, subQ, AM and PM).

Patients who achieve threshold serum levels of FSH at 50 IU, 75 IU, 150 IU, 200 IU or other daily FSH dosages during Phase I of Cycle 2 will receive a ramped-down regimen of rFSH dosages during Phase II of Cycle 2 that is analogous to the one described above. These patients may also receive daily dosage of hCG (10 IU) and luteal phase prometrium support (200 mg BID) as the patients with who reach the FSH threshold at a dose of 150 IU FSH.

Patients are given ultrasound evaluations starting 6 days after their first FSH injection, and will be prescribed estradiol, FSH measurements, and additional ultrasounds every several days thereafter. This will permit the physician to monitor for a normal rate of follicular growth (1-2 mm/day), count the number of growing follicles, and provide individual adjustments in medication dosages to accommodate patient metabolism of medication. Ultrasound measurements will also permit determination of when a follicle is mature (18 mm or more). Administration of FSH may be extended beyond day 18, until the mature follicle is detected, whereupon the 150 IU rFSH+10,000 IU hCG injection will be administered. In a modification of this protocol, rFSH injections are supplemented daily throughout the menstrual cycle with 37.5 amp of rLH (Luveris) 2× per day (subQ injection). Prometrium capsules, vaginally administered 200 mg BID, are added to the luteal phases of cycles 2, 3, and 4 if needed, as determined by luteal phase measurements in a previous cycle.

Cycle 3: Pre-cycle

Tests for serum hormones are performed at regular intervals throughout this cycle (as well as the subsequent cycles), and administration of leuprolide, rFSH, hCG, and letrozole (for AI-HNT patients) are performed as described for Cycle 2, with adjustments made based on these serum measurements in order to accommodate individual patient metabolism of drugs, as described above to approximate young hormonal levels. The longer ramp-up testing phase that was performed in Phase I of cycle 2 to determine FSH dosage required to achieve threshold levels need not be repeated in Cycle 3 or Cycle 4. By way of example the following protocol would be given, assuming that 100 IU FSH/day was the initial dose that had been found to achieve threshold serum FSH levels conducive to follicular development:

Days 2-4: 100 IU rFSH (50 IU, 2×/day, subQ, AM and PM), with or without daily hCG supplementation (10 IU/day).

Days 5-7: 75 IU rFSH (37.5 IU FSH/day, 2×/day, subQ, AM and PM), with or without daily hCG supplementation (10 IU/day).

Days 8-14: 50 IU rFSH (25 IU FSH/day, 2×/day, subQ, AM and PM), with or without daily hCG supplementation (10 IU).

Day 14 (exact day occurs when follicle reaches approximately 18 mm): 150 IU rFSH+10,000 units of hCG (Pregnyl) shot timed to be approximately 36 hours prior to scheduled retrieval time)

Days 15-25: no FSH

Days 26-day 1 of NEXT cycle: 50 IU rFSH/day (25 IU FSH, 2×/day, subQ, AM and PM)

Day 2 of NEXT CYCLE: 100 IU rFSH (75 IU rFSH, 2×/day, subQ, AM and PM)—then proceed exactly the same way in the subsequent cycles as described above, with adjustments in individual dosages as needed to accommodate patient metabolism of medications.

Cycle 4: The Test Cycle

1. Hormone tests, and administration of leuprolide, FSH, and letrozole will be performed throughout the follicular phase as described in Cycle 3, with adjustments made to accommodate individual patient metabolism of drugs as described above to approximate young hormonal levels.

2. Monitor progression of follicular growth when patient is in mid-cycle by performing ultrasounds in mid-follicular phase starting day 7 of the cycle. Perform ultrasounds frequently beginning in the mid-follicular phase until dominant follicle reaches 18-19 mm.

3. Induce ovulation by subcutaneous injection of 10,000 international units of highly purified hCG (Pregnyl). 150 IU of FSH will also be administered as a single dose on this day, as will 10 mg of letrozole. Pregnancy will not be attempted by intercourse or intrauterine insemination.

4. 36 hours later, perform transvaginal ultrasound-guided oocyte aspiration under light intravenous sedation to retrieve the oocyte from each patient. Oocytes and the surrounding follicular fluid will be retrieved at this time. In vitro fertilization will be performed. Oocytes will undergo in vitro fertilization with the male partner's sperm. Polar bodies from embryos grown in the laboratory to the pre-implantation stage are then biopsied to remove polar bodies I and II, which are analyzed for chromosome copy number by CGH, FISH, or other methods of analyses. Embryos after biopsy are transferred back into the uterus. Luteal phase progesterone support is provided (200 mg prometrium BID daily vaginal administration). rFSH at a dosage of 37.5 IU 2x/day (AM and PM) will be given starting on day 26 until day 28, whereupon a pregnancy test will be administered patients will be given a pregnancy test approximately 15 days after retrieval. Patients with a positive pregnancy test are followed for evidence of clinical progression and viability of the pregnancy, according to standard of care for OB/Gyn patients in early pregnancy.

Cycle 5: Pregnancy Test Cycle

Patients who do not get pregnant in Cycle 4 will be provided an opportunity attempt pregnancy in a fifth cycle, Hormone administration will be performed as described in cycle 3 using optimized dosages and regular serum hormone and ultrasound monitoring. This hormonal treatment will be started as described for Day 1 of the AI-HNT therapy. Administration of hCG to trigger ovulation will be performed as proscribed in cycle 4 once follicles mature to 18-19 mm. Luteal phase progesterone support is provided (200 mg prometrium BID daily vaginal administration). rFSH at a dosage of 37.5 IU 2x/day (AM and PM) will be given starting on 26 until day 28, whereupon a pregnancy test will be administered patients will be given a pregnancy test approximately 15 days after retrieval. Patients with a positive pregnancy test are followed for evidence of clinical progression and viability of the pregnancy, according to standard of care for OB/Gyn patients in early pregnancy.

EXAMPLE 6

Patients Groups for AI-Hormone Normalization Therapy

All patients eligible for the treatment are aged 35 and older. This test group includes patients with a history of idiopathic infertility, premature ovarian failure, diminished ovarian reserve, or repeated implantation failure. Other candidates for the therapy are women with 1 or more documented autosomal trisomic conceptus or 2 or more miscarriages that have not been karyotyped. Patients who have had Down, Patau, and Edward syndrome pregnancies are also included. Patients will present with high basal estradiol or high estradiol and high FSH in a cycle prior to the hormone adjustment cycle (see the aromatase inhibitor hormone normalization therapy proposal and FIG. 6).

EXAMPLE 7

Therapeutic Regimen for Pregnancy Studies in AI-HNT Patients.

Figure 6:
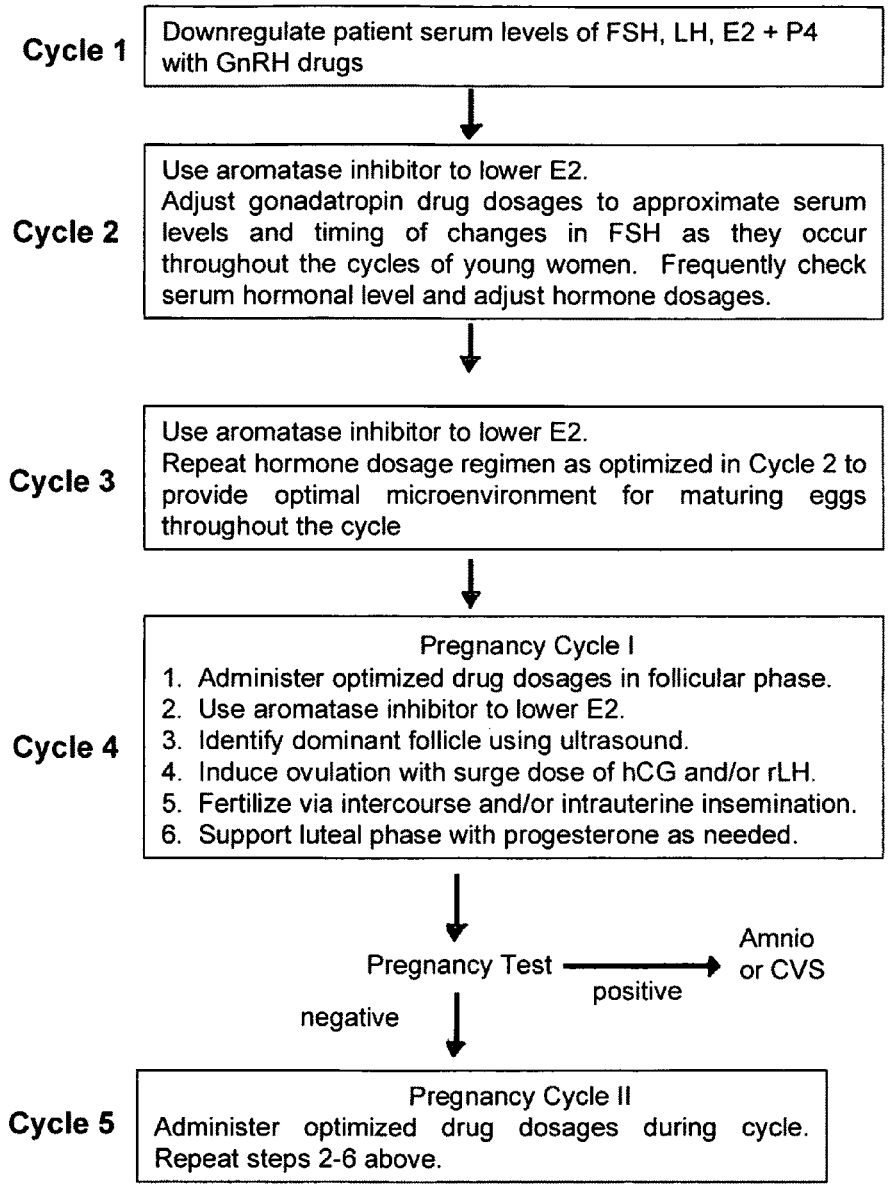
FIG. 6 outlines the clinical protocol for AI-HNT therapy for women with high serum estradiol. As for HNT, patients receiving AI-HNT are administered a series of hormonal treatment cycles four to five menstrual cycles in duration. The regimen of hormonal treatments contains GnRH, GnRH agonist and/or or GnRH antagonist; FSH in doses that vary with the phase of the menstrual cycle, with or without hCG and/or LH supplementation; follicular phase aromatase inhibitor drug (AI) that may vary in dosage with the phase of the menstrual cycle; a bolus injection of LH and/or hCG to trigger ovulation; and progesterone as needed to provide adequate luteal phase support.

Patients undergo basal hormone measurements, followed by pituitary downregulation with GnRH, GnRH agonist, or GnRH antagonist, followed by several successive cycles of hormone normalization treatment with low doses of reproductive hormones and AI designed to approximate those of a young woman on each day of the cycle (FIG. 6). Levels of estradiol and FSH are measured regularly throughout the regimen. Levels of progesterone are measured several times in the luteal phase of each cycle as well. Patients will then attempt to get pregnant by natural conception and/or by intrauterine insemination. No in vitro fertilization is required for these studies.

Specific HNT and AI Drugs in Pregnancy Trial.

The protocol provided is a specific example to teach the art of the AI-HNT therapy for patients attempting pregnancy. The therapy may also be performed using doses of the other medications listed in Table 1 that give a comparable range of bio-activity for that class of medication.

Cycle 1: Downregulation Cycle

1. Monitor FSH and LH, P4, and E2 levels by frequent serum measurements.
2. On day 21 of the cycle, initiate administration of leuprolide, 1 mg/day subcutaneous injection until the beginning of the Cycle 2.

Cycle 2: Drug Adjustment Cycle

1. Assess downregulation 10-14 days after the first leuprolide dose by vaginal ultrasound and measurement of serum estradiol and FSH.
2. Continue frequent measurements of patient's FSH and E2 levels throughout Cycle 2.
3. Day 1 of cycle 2 is defined as the day on which FSH injections are started (see below for protocol). On Day 1 of cycle 2, reduce dose of leuprolide from 1 mg/day as given in cycle 1, down to 0.5 mg/day (subQ). 0.5 mg/day leuprolide administration will continue uninterrupted throughout the entirety of cycles 2 and 3, and until shortly prior to the time of retrieval in cycle 4.
4. Start FSH treatments. FSH will be human menopausal gonadotropin, or will be recombinant human FSH (rFSH, follitropin alpha) or highly purified FSH, with or without prescription of daily supplementary LH activity medication (e.g., hCG).

The FSH treatment regimen in this protocol is designed to approximate the levels of FSH in the young female throughout the cycle. To accomplish this, Cycle 2, unlike the other HNT treatment cycles, is comprised of two phases. Phase I is designed to identify the minimal dose of FSH required for the patient to achieve threshold levels of FSH conducive to follicular development. Phase II of cycle 2, and Cycles 3 and 4, are designed to approximate normal FSH levels throughout the menstrual cycles in the patient. This protocol design will minimize the likelihood of administering dosages of FSH that may lead to levels of FSH that fall above or below the range of normal FSH levels for a young and fertile woman.

For AI HNT patients, Phase I of cycle 2 will also serve as the initial optimization phase for administration of AI medication to achieve young E2 levels. Phase II of cycle 2, and Cycles 3 and 4, are designed to approximate normal FSH and E2 levels throughout the menstrual cycles in the patient with high estradiol and normal or high FSH. This protocol design will diminish the likelihood of administering dosages of FSH and AI that may lead to levels of FSH and E2 that fall above or below the ranges of normal FSH and E2 that are found in a young and fertile woman.

Phase I of Cycle 2: Finding a Threshold Dosage of FSH for Each Patient

The first day of FSH injection is defined as Day 1 of Cycle 2. Patients will administer subQ injections of FSH in a ramp-up fashion in the early phase of cycle 2, followed by a ramp-down phase of the protocol later in cycle 2. This will be with or without subQ co-administration of 10 international units of supplementary hCG (total 10 IU per day; Pregnyl). Patients will continue daily injections of GnRH agonist for the duration of the follicular and luteal phases of the cycle, and will perform the following schedule for injections of FSH:

Day 1: Patients will receive 50 IU/day sc of FSH starting on day one of FSH treatment (25 IU AM and PM). Patients will be treated in this way for 4 days.

Day 5: Patients will undergo serum quantitation of FSH levels. FSH quantitation will be performed on day 5 because it takes 4 days for steady-state levels of FSH to be established in a woman being given daily FSH injections at a given dosage. If FSH level does not meet or exceed the threshold FSH level, the dosage of FSH will be increased to 75 IU/day (37.5 IU AM and PM) for 4 days.

Day 9: Quantitate serum FSH levels. If FSH level does not meet or exceed the threshold FSH level, the dosage of FSH will be increased to 100 IU rFSH/day (50 IU AM and PM) for 4 days.

Day 13: Quantitate serum FSH levels. If FSH level does not meet or exceed the threshold FSH level, the dosage of FSH will be increased to 150 IU rFSH/day (75 IU AM and PM) for 4 days.

Day 17: Quantitate serum FSH levels. If FSH level does not meet or exceed the threshold FSH level, the dosage of FSH will be increased to 200 IU rFSH/day (100 IU AM and PM) for 4 days.

This pattern will be continued as needed in FSH increments until the serum FSH threshold level is met for that specific patient.

Phase II of Cycle 2. Hormone Normalization Starting with the Threshold Dosage and Proceeding Through the Cycle Once the serum FSH threshold level is reached, the daily dosage will be decreased in several phases to emulate the normal hormonal changes across the cycle that occur in a young woman. For instance, take the example of a patient who reaches the threshold FSH level at daily FSH dosage of 100 IU/day as measured on day 13. For a patient who responds in this manner, the ramping up of dosages would stop on this day, and the protocol would then proceed as explained below.

Days 13-15: 75 IU rFSH/day (37.5 IU FSH 2×/day, subQ, AM and PM), with or without daily hCG supplementation (10 IU total).

Days 16-18: 50 IU rFSH/day (25 IU FSH 2×/day, subQ, AM and PM), with or without daily hCG supplementation (10 IU total).

Day 19 (this is an approximation; exact day occurs when follicle reaches approximately 18 mm): 150 IU rFSH+10,000 IU of hCG (75 IU FSH subQ in PM; +10,000 IU highly purified hCG (Pregnyl) PM shot timed to be 36 hours prior to scheduled retrieval time). Daily administration of FSH doses may be extended until the mature follicle is detected.

Days 20-30: no FSH

Days 31 to day 1 of NEXT cycle (i.e., first day of menses): 50 IU rFSH (25 IU FSH 2×/day, subQ, AM and PM)

Day 2 of NEXT CYCLE (Cycle 3): 100 IU (50 IU FSH/day 2×/day, subQ, AM and PM).

Patients who achieve threshold serum levels of FSH at 50 IU, 75 IU, 150 IU, 200 IU or other daily FSH dosages during Phase I of Cycle 2 will receive a ramped-down regimen of rFSH dosages during Phase II of Cycle 2 that is analogous to the one described above. These patients may also receive daily dosage of hCG (10 IU) and luteal phase prometrium support (200 mg BID) as the patients with who reach the FSH threshold at a dose of 150 IU FSH.

Patients are given ultrasound evaluations starting 6 days after their first FSH injection, and will be prescribed estradiol, FSH measurements, and additional ultrasounds every several days thereafter. This will permit the physician to monitor for a normal rate of follicular growth (1-2 mm/day), count the number of growing follicles, and provide individual adjustments in medication dosages to accommodate patient metabolism of medication. Ultrasound measurements will also permit determination of when a follicle is mature (18 mm or more). Administration of FSH may be extended beyond day 18, until the mature follicle is detected, whereupon the 150 IU rFSH+10,000 IU hCG injection will be administered. In a modification of this protocol, rFSH injections are supplemented daily throughout the menstrual cycle with 37.5 amp of rLH (Luveris) 2× per day (subQ injection). Prometrium capsules, vaginally administered 200 mg BID, are added to the luteal phases of cycles 2, 3, and 4 if needed, as determined by luteal phase measurements in a previous cycle.

Cycle 3: Pre-cycle

Tests for serum hormones are performed at regular intervals throughout this cycle (as well as the subsequent cycles), and administration of leuprolide, rFSH, hCG, and letrozole (for AI-HNT patients) are performed as described for Cycle 2, with adjustments made based on these serum measurements in order to accommodate individual patient metabolism of drugs, as described above to approximate young hormonal levels. The longer ramp-up testing phase that was performed in Phase I of cycle 2 to determine FSH dosage required to achieve threshold levels need not be repeated in Cycle 3 or Cycle 4. By way of example the following protocol would be given, assuming that 100 IU FSH/day was the initial dose that had been found to achieve threshold serum FSH levels conducive to follicular development:

Days 2-4: 100 IU rFSH (50 IU, 2×/day, subQ, AM and PM), with or without daily hCG supplementation (10 IU/day).

Days 5-7: 75 IU rFSH (37.5 IU FSH/day, 2×/day, subQ, AM and PM), with or without daily hCG supplementation (10 IU/day).

Days 8-14: 50 IU rFSH (25 IU FSH/day, 2×/day, subQ, AM and PM), with or without daily hCG supplementation (10 IU).

Day 14 (exact day occurs when follicle reaches approximately 18 mm): 150 IU rFSH+10,000 units of hCG (Pregnyl) shot timed to be approximately 36 hours prior to scheduled retrieval time)

Days 15-25: no FSH

Days 26-day 1 of NEXT cycle: 50 IU rFSH/day (25 IU FSH, 2×/day, subQ, AM and PM)

Day 2 of NEXT CYCLE: 100 IU rFSH (75 IU rFSH, 2×/day, subQ, AM and PM)—then proceed exactly the same way in the subsequent cycles as described above, with adjustments in individual dosages as needed to accommodate patient metabolism of medications Cycle 4: The Test Cycle 1. Hormone tests, and administration of leuprolide, FSH, and letrozole will be performed throughout the follicular phase as described in Cycle 3, with adjustments made to accommodate individual patient metabolism of drugs as described above to approximate young hormonal levels.

2. Monitor progression of follicular growth when patient is in mid-cycle by performing ultrasounds in mid-follicular phase starting day 7 of the cycle. Perform ultrasounds frequently beginning in the mid-follicular phase until dominant follicle reaches 18-19 mm.
3. Induce ovulation by subcutaneous injection of 10,000 international units of highly purified hCG (Pregnyl). 150 IU of FSH will also be administered as a single dose on this day, as will 10 mg of letrozole. Pregnancy will not be attempted by intercourse or intrauterine insemination.
4. Approximately 32-38 hours later, perform intrauterine insemination with partner's sperm. Luteal phase progesterone support is provided as needed with prometrium 200 mg daily BID.
5. Resume rFSH treatments at a dose of 37.5 IU 2×/day (AM and PM) sc starting day 26. Patient is given a pregnancy test 15 days after intrauterine insemination. Patients with a positive pregnancy test are followed for evidence of clinical progression and viability of the pregnancy, according to standard of care for OB/Gyn patients in early pregnancy.

Cycle 5: Pregnancy Test Cycle

Patients who do not get pregnant in Cycle 4 will be provided an opportunity attempt pregnancy in a fifth cycle, Hormone administration will be performed as described in cycle 3 using optimized dosages and regular serum hormone and ultrasound monitoring. This hormonal treatment will be started as described for Day 1 of the HNT therapy. Administration of hCG to trigger ovulation will be performed as proscribed in cycle 4 once follicles mature to 18-19 mm. Luteal phase progesterone support is provided (200 mg prometrium BID daily vaginal administration). Patients will be given a pregnancy test approximately 15 days after intrauterine insemination. Patients with a positive pregnancy test are followed for evidence of clinical progression and viability of the pregnancy, according to standard of care for OB/Gyn patients in early pregnancy.

EXAMPLE 8

Mouse Studies

There are no ideal rodent models for human female reproductive aging. Most strains of mice do not display age-related aneuploid defects to the extent that humans do. A senescence-accelerated strain of mice called SAM mice come closer to human reproductive aging than most other rodent models. It was determined that 7-8 month old female SAM8 mice have significantly higher levels of FSH than 2-3 month old mice female SAM8 mice (quantitative FSH value of 3.5 ng/ml for young mice vs. 8 ng/ml for old mice. It also was determined that ovulated oocytes from female SAM8 mice have three-fold higher incidence of chromosome and spindle disorganization, both in the meiosis I and meiosis II stages of maturation, i.e., 59% chromosome disorganization vs. 20% in old vs. young SAM8 mice, and 41% vs. 14% spindle disorganization in old vs. young SAM8 mice (Young: FIGS. 7A-7E; Old: FIGS. 7F-7M). The latter observation is in agreement with published work by Liu and Keefe with female SAM1 mice. Taken together the FSH data and the chromosome and spindle data indicate that the SAM8 model is a good mouse model for female reproductive aging in which to test hormone normalization therapy. In addition it was determined that 9 month old CBA/Ca female mice have markedly elevated FSH levels compared to 2-4 month old female CBA/Ca mice. Ovulated oocytes from 9 months old CBA/Ca mice have high aneuploidy incidence whereas oocytes from 2-4 month old CBA/Ca mice have low aneuploidy incidence in published studies.

Hormone normalization therapy in mice is performed as follows. Hormone levels in young and old SAM8 or CBA/Ca female mice are measured throughout the estrous cycle, and dosages needed to recreate young and old hormone profiles are determined. Hormone normalization therapy is performed by administration of leuprolide, FSH, and chorionic gonadotropin or LH according to dosages that create young hormone profile in old mice and an old hormone profile in young mice. Young and old untreated mice will constitute control groups. Oocytes are retrieved after inducing ovulation by injection of LH or hCG, and analyzed for chromosome and spindle organization, or by array comparative genomic hybridization.

EXAMPLE 9

Human Studies

The human studies are aimed at women between ages of 38-43. These subjects will have high FSH and/or estradiol. In addition, they will have a history of previous miscarriage, or previous history of infertility and recurrent implantation failure (RIF). Previous miscarriage patients have had one or more documented autosomal trisomy or two or more losses or stillborn or liveborn aneuploid conceptuses. This group shall include subjects who have had Down, Edward, or Patau Syndrome pregnancies.

Figure 8:
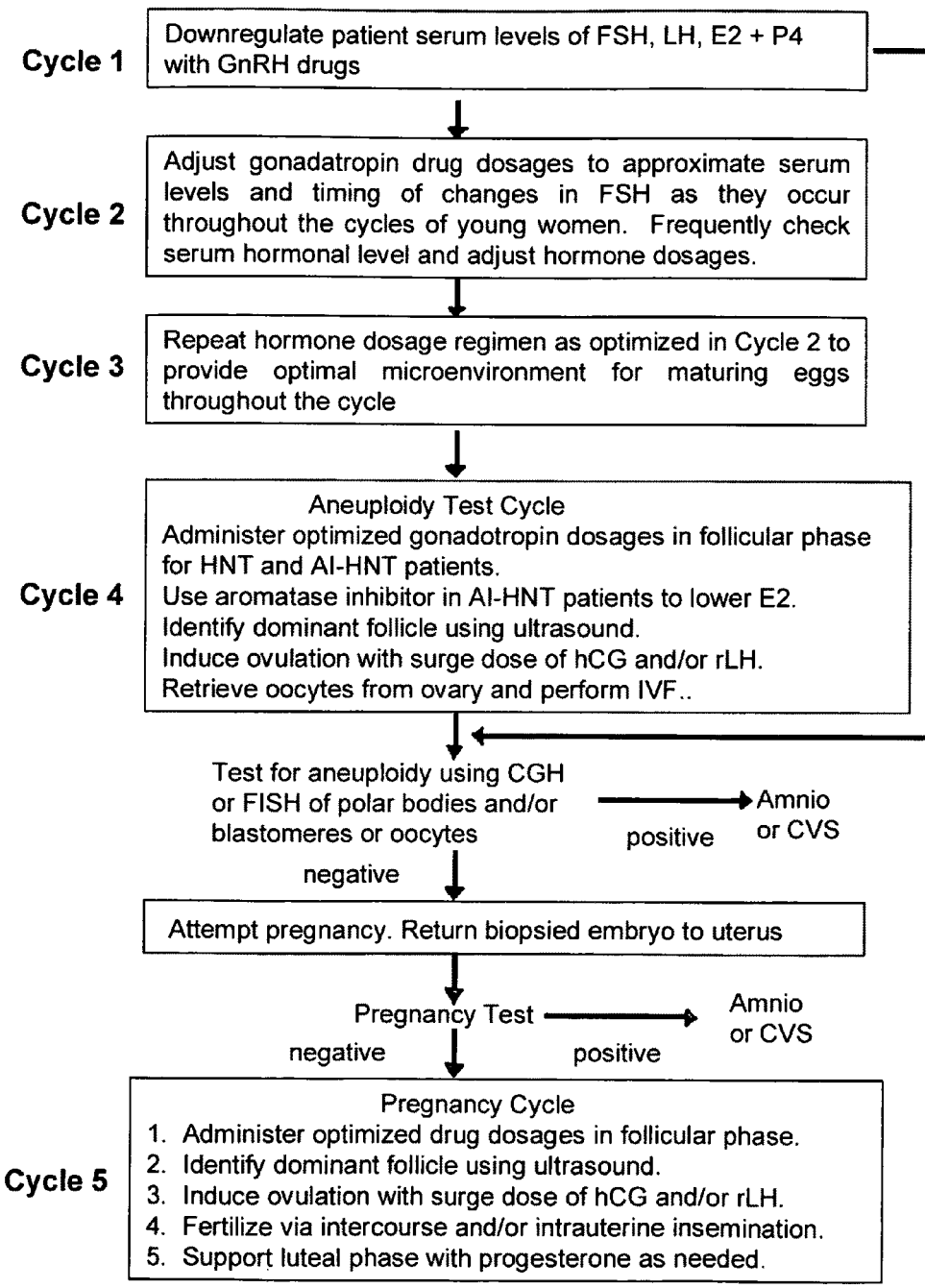
FIG. 8 outlines the clinical protocol for the Aneuploidy Trials, as applied to both HNT and AI-HNT patients. Unlike the pregnancy trials, patients in the aneuploidy trials undergo oocyte retrievals in Cycles 1 and 4. The oocyte retrieved in cycle 4 is fertilized in vitro (IVF) with male partner's sperm. Karyotypes of retrieved oocytes from Cycle 1 (before treatment) and biopsied cells from preimplantation embryos from Cycle 4 (after treatment) are compared to demonstrate reduced aneuploidy incidence after HNT and AI-HNT. This is followed by pregnancy attempts in cycle 4, and if patients do not get pregnant in cycle 4, in cycle 5.

There are two trials. One trial shall consist of patients who shall donate oocytes procured before hormone normalization therapy, to be compared to genetic material biopsied from preimplantation embryos for chromosomal analysis after hormone normalization therapy. This trial assesses the extent to which hormone normalization therapy prevents aneuploidy in these patients (Aneuploidy Clinical Trial). The second trial consists of patients who will not undergo oocyte retrieval or IVF. These patients seek to get pregnant during hormone normalization therapy (Pregnancy Clinical Trial). The objective of this trial shall be to use hormone normalization therapy to increase the pregnancy success rates for women with previous miscarriages and previous infertility. Both these trials are outlined below. See FIG. 8 for an outline of the clinical protocol.

Aneuploidy Clinical Trial

Decreased aneuploidy in oocytes of advanced maternal age women following hormone normalization therapy is measured. The subjects for this trial are either advanced maternal age women who have experienced previous miscarriages (PM group) or advanced maternal age-women who are infertile due to recurrent implantation failure (RIF group).

Inclusion Criteria for Aneuploidy Studies

PM Group for Aneuploidy Trial

Inclusion Criteria for Female Patients.

Female Patients for all aneuploidy trial subjects of the study should have:
1. Ages range from 3843 years
2. Day 3 FSH greater than or equal to 15 IU and/or (for AI-HNT patients) day 3 E2 level greater than or equal to 80 pg/ml
3. Regular ovulatory menstrual cycles occurring every 24-35 days
4. Euthyroid or corrected hypothyroidism with more than 1 month's time between correction of thyroid condition and initiation of Cycle 0 (Baseline hormone measurement cycle)
5. Normoprolactinemia or Hyperprolactinemia Treated Successfully 30 Days or More Prior to Initiation of Participation in Trial.

Male Patients for all Trials of the Study (PM and RIF Patients)
1. Sperm sample obtainable from ejaculate.
2. Total motile sperm count greater than 10,000,000/ejaculate and normal morphology by WHO or Krueger's criteria.

Previous Miscarriage Group for Aneuploidy Trial
  One or more documented trisomic conceptuses (autosomal aneuploidy) or two or more documented pregnancy losses without karyotyping.

Female RIF Infertility group for aneuploidy trial
  3 or more failed IVF attempts or failure to get pregnant after transfer of more than 10 morphologically normal embryos in IVF Basic Trial Design:
  Patients from the PM and RIF group populations with high FSH and normal estradiol are given hormone normalization therapy. Patients from the PM and RIF group populations with normal or high FSH and high estradiol are given hormone normalization therapy plus aromatase inhibitor ("AI") to lower the estradiol levels.
  This drug regimen is called "AI-hormone normalization therapy." Therefore there are four treatment groups in this study:
  Treatment Group 1a: PM patients with high FSH and normal E2-hormone normalization therapy;
  Treatment Group 1b: RIF patients with high FSH and normal E2-hormone normalization therapy;
  Treatment Group 2a: recurrent miscarriages patients with normal or high FSH and high E2—aromatase inhibitor-hormone normalization therapy;
  Treatment Group 2b: recurrent implantation failure patients with normal or high FSH and high E2—aromatase inhibitor-hormone normalization therapy.
  Patients in groups 1a+1b and in groups 2a+2b will receive identical treatment, but data from the four test groups are analyzed separately.

Exclusion Criteria for Female Patient
1. BMI below 19 or above 26.
2. Medical conditions contraindicating pregnancy.
3. Abnormal maternal karyotype.
4. Previous chemotherapy or pelvic radiation therapy for cancer; prior reproductive tract or breast cancer.
5. Individuals with greater than a 5-pack year history of tobacco smoking
6. Caffeine intake in excess of 4 servings a day.
7. Positive for endometritis within 30 days of participation in the study. Patients can participate if their endometritis has been treated and 30 or more days have elapsed prior to participation in the study.
8. Abnormal uterine morphology (submucosal fibroids, intramural fibroids exceeding 5 cm in largest diameter; uncorrected congenital uterine abnormalities excluding arcuate nucleus and excluding septum less than one cm; Asherman's syndrome).
9. Patients with a prior history of antiphospholipid syndrome or inherited thrombophilias known to be associated with recurrent pregnancy loss will be excluded. Patients seropositive for these conditions will also be excluded. Patients with known mutational heterozygosity of genes for these syndromes or with mutations in methylene tetrahydrofolate reductase will not be excluded.
10. Patients that must take drugs that are contraindicated for pregnancy must be excluded. Patients who take these medications electively should terminate their use 30 days before initiation of hormonal measurements in Cycle 0. The purpose of this exclusion is to promote the health of the prospective mother and her baby.
11. Treatment with antibiotics or antimycotics within thirty days prior to entry into study.
12. Use of recreational drugs within 30 days of the start of the first day of Cycle 0 or during the study.
13. More than ten alcoholic beverages per week 30 days or less prior to the initiation of the study or during the study.
14. Steroidal or gonadotrophic hormonal treatments within 30 days of initiation of Cycle 0 measurements or during the HNT treatments.

Exclusion Criteria for Male Patient
1. Abnormal paternal karyotype.
2. History of vasectomy reversal.
3. Cessation of smoking less than 80 days prior to anticipated date of semen sample procurement
4. Treatment with sulphasalazine (used to treat inflammatory bowel disease) or cyclosporin (immunosuppressant medication) less than 80 days before sperm sample will be procured for fertilization in the study.
5. Alcohol consumption in excess of ten alcoholic beverages per week within 80 days of the time that the patient will contribute a semen sample.
6. Recreational drug use less than 80 days before sperm sample will be procured for fertilization in the study.
7. Use of anabolic steroids or testosterone, estrogenic compounds, FSH, or LH 80 or more days prior to the expected day that sperm sample will be procured for fertilization. Note that inclusion and exclusion criteria for the clinical trials are more restrictive than criteria used to evaluate patients for HNT in a conventional clinical treatment context.

Basic Strategy of the Therapy for the Aneuploidy Trial
  The hormone normalization therapy and aromatase inhibitor-hormone normalization therapy protocols will consist of a basal measurement cycle, plus a succession of three hormonal treatment cycles. Patients in the mid-luteal phase of cycle 1 of the aneuploidy trial will undergo retrieval of oocytes prior to hormonal treatment, and will undergo a second retrieval in cycle 4, after several rounds of hormonal treatment.
  Cycle 0 (Basal Hormone Measurement Cycle). This is an initial cycle in which levels of gonadotropin and steroid hormones are measured in untreated patients throughout the cycle. No hormone treatments are to be given in this cycle (Cycle 0 is an experimental cycle only and is not therapeutic).
  Cycle 1 (Control Downregulation Cycle). Patients undergo no treatment in the follicular phase of the cycle. Oocytes and their polar bodies are retrieved after ovulation induction with hCG and analyzed for aneuploidy. Patients in the mid-luteal phase of the cycle initiate downregulation with gonadotropin releasing hormone (GnRH), GnRH agonist or GnRH antagonist.
  Cycle 2 (Drug Adjustment Cycle). Dosage of FSH and AI are adjusted to approximate previously published ranges in serum FSH and E2 levels for young fertile women, administering the drug doses that would be expected to approximate young target levels. Frequent monitoring of hormonal levels throughout the cycle is performed so that doses can be further adjusted to individual differences in patient metabolism of medication.
  In Cycle 3 (Pre-Cycle) optimized dosages established in Cycle 2 are again utilized to equilibrate advanced maternal age patients to a young hormonal milieu.
  In Cycle 4 (Actual Test Cycle) the dosage regimens used in Cycle 3 are provided in the follicular phase. Oocyte(s) is retrieved, and fertilized in vitro with male partner's sperm sample. Fertilized embryos are developed to the preimplantation stage and polar bodies I and II and/or blastomeres(s) are biopsied. The embryo after biopsy is transferred back into the uterus of the mother.

Retrieved oocytes from untreated Cycle 1 and polar bodies biopsied from preimplantation embryos obtained by IVF from Cycle 4 are analyzed for the incidence of aneuploidy. Patients serve as their own controls in this study since the incidence of aneuploidy in the oocytes is compared between material retrieved from patients before and after hormone treatments. This longitudinal data gathering strategy is expected to be more powerful statistically than inclusion of separate untreated control groups. Patients will also have the opportunity to perform Cycle 5, a pregnancy test cycle during which IUI will be performed instead of IVF.

AI-hormone Normalization Therapy

The aromatase inhibitor-hormone normalization therapy patients receive hormone normalization therapy treatments, consisting of a basal hormone measurement cycle and a series of three hormonal treatment cycles. The aromatase inhibitor-hormone normalization therapy regimen contains an aromatase inhibitor drug during cycles 2 and 3 and 4.

Detecting Chromosomal Aneuploidy in Oocytes, and Polar Bodies of Oocytes, and Embryos.

The chromosomal aneuploidy in biopsied oocytes and embryos is examined by either one or both of the following methods: (1) "Comparative Genomic Hybridization" (CGH), which detects abnormalities in all 23 human chromosomes, and/or (2) "multi-color fluorescence in situ hybridization" (FISH), which detects abnormalities in only the tested chromosomes, generally the most commonly aneuploid chromosomes. Comparative Genomic Hybridization has a higher success rate than fluorescence in situ hybridization in picking up all abnormalities because it looks at all chromosomes. Also, the Comparative Genomic Hybridization method is more reliable and less prone to loss of information.

The Pregnancy Trial

This trial demonstrates that hormone normalization therapy decreases the incidence of aneuploid conceptions and increases the rates of pregnancy and live births. The subjects for this trial are either advanced maternal age women who have experienced previous miscarriages (PM group) or advanced maternal age women that are infertile due to recurrent implantation failure (RIF group). The inclusion and exclusion criteria for the PM and RIF patients in the pregnancy trial and their male partners are the same as those for the aneuploidy trial, with the additional provision that the female patients must have documented evidence of patency of at least one fallopian tube, since they will not be undergoing IVF.

Basic Trial Design: A Randomized Pregnancy Trial

Female patients from the PM and RIF populations will sort into treatment groups, Treatment groups will be randomly assigned to experimental and control groups. Experimental groups will be given HNT they have high FSH and normal E2, or AI-HNT, if they have high E2 (and normal or high FSH), Control groups will be given controlled ovarian hyperstimulation (COHS) regimen consisting of high FSH dosages for 10-14 days. This is a traditional regimen used for infertile patients to try to improve their chances of getting pregnant. This study compares the efficacy of the known treatments to these new treatments.

Test Group 1: PM patients with high FSH and normal E2—hormone normalization therapy
Control Group 1: PM Patients with High FSH and Normal E2—COHS
Test Group 2: RIF patients with high FSH and normal E2—hormone normalization therapy.
Control Group 2: RIF Patients with High FSH and Normal E2—COHS.
Test Group 3: PM patients with high E2 and normal or high FSH—aromatase inhibitor-hormone normalization therapy.
Control group 3: PM Patients with high E2 and normal or high FSH and—COHS
Test Group 4: RIF patients with high E2 and normal or high FSH—aromatase inhibitor-hormone normalization therapy.
Control Group 4: RIF Patients with high E2 and normal or high FSH—COHS.

Basic Strategy of the Therapy for the Pregnancy Trial

Like the aneuploidy trial, the hormone normalization therapy and aromatase inhibitor-hormone normalization therapy pregnancy trials consist of a basal measurement cycle, plus a succession of three hormonal treatment cycles, each one menstrual cycle in duration.

Cycle 0 (Basal Hormone Measurement Cycle). This is an initial cycle in which levels of gonadotropin and steroid hormones are measured in untreated patients throughout the cycle. No hormone treatments are to be given in this cycle (Cycle 0 is an experimental cycle only and is not therapeutic).

Cycle 1 (Control Downregulation Cycle). Patients undergo no treatment until day 21 of the cycle, whereupon gonadotropin releasing hormone agonist (GnRH) is initiated for the duration of the therapy. A single bolus injection of long-acting Depot-lupron, or daily GnRH sc injections of GnRH agonist will be given. Alternatively, GnRH antagonist may be used Cycle 2 (Drug Adjustment Cycle). Levels of hormones are targeted according to values that are in normal ranges for young women at the various phases of the menstrual cycle, administering the doses of reproductive hormones that would be expected to approximate target levels. Frequent monitoring of hormonal levels are also performed so that doses can be further adjusted to individual differences in patient metabolism of medication.

In Cycle 3 (Pre-Cycle) optimized daily dosages are utilized to equilibrate advanced maternal age patients to a young hormonal milieu.

In Cycle 4 (Actual Pregnancy Cycle) the dosage regimens used in Cycle 3 are again provided, and the cycle by insemination of the patient is terminated, either by intercourse with the husband or by intrauterine insemination (IUI). Patients are provided luteal phase support with progesterone as required.

At the time of expected menses for that cycle, patients are given a pregnancy test. If the patient has a positive pregnancy test, their pregnancy is followed to know the outcome of the pregnancy. Patients who do not get pregnant will have the opportunity to perform a second pregnancy test cycle, Cycle 5, during which the HNT hormonal regimen is again followed and IUI is performed. As for cycle 4, At the time of expected menses for that cycle, patients are given a pregnancy test. If the patient has a positive pregnancy test, their pregnancy is followed to know the outcome of the pregnancy. All miscarriages and liveborns are karyotyped with parental approval.

The following references were cited herein:
1. Schon E A, et al., Hum. Reprod. 15: 160-72, 2000
2. Van Blerkom J V, et al., Hum. Reprod 12: 1047-55, 1997
3. Van Blerkom J V Assisted. Reprod. And Genet. 15: 226-34, 1998
4. Fauser, et al., Reproductive Medicine, Parthenon Publishing Group, 2003
5. Strauss and Barbieri, Yen and Jaffe's Reproductive Endocrinology, Elsevier-Saunders, 2004
6. Thomas F H, et al., Hum Reprod Update 9: 541-55, 2003

7. Britt K L, et al., Biol. Reprod. 71: 1712-23, 2004
8. Tesarick J, Mendoza C. Hum Reprod. Update 3: 95-100, 1997
9. Li, Q, et al., J. Reprod. Dev. 50: 305-15, 2004
10. Beker-van Woudenberg A R, et al., Biol. Reprod 70: 1465-74, 2004
11. Hall, J E. Endocrinol Metab. Clin N. Am. 637-59, 2004
12. Klein, N A et al., J. Clin Endocrinol Metab 81: 1946-51, 1996
13. Burger H G, et al., Climacteric 3: 17-24, 2000
14. Levi A J, et al., Fert. And Steril. 76: 666-9, 2001
15. Gurbuz B, et al., Arch. Gynecol Obstet 270: 37-9, 2004
16. Trout S W, Seifer D B. Fert. Steril 74: 335-7, 2000
17. Nasseri A., et al., Fertil. And Steril. 71: 715-8, 1999
18. Kline J., et al., Hum. Reprod. 19: 1633-43, 2004
19. Montfrans J M, et al. The Lancet 353, 1853-4, 1999
20. Nasseri A. et al., Fert and Steril 71: 715-8, 1999
21. McTavish K J, et al. Endocrionology 148: 4432-9, 2007
22. van der Steeg J W. Et al. J. Clin Endocrinol Metab. 92: 2163-8, 2007
23. van Rooij I A, et al. Fert and Steril 81: 1478-85, 2004
24. Levi A J, et al. Fert and Steril 76: 666-9, 2001
25. Esposito M A, et al. Hum Reprod. 17: 118-23, 2002
26. Akande V A, et al. Hum Reprod, 17: 2003-8, 2002
27. van Rooij, I A J, et al. Reprod Biomed Online 12: 192-90, 2006
28. Pampiglione, et al., Check, J H, et al. Fert and Steril. 50: 603-6, 1988
29. Gynecol Obstet. Invest. 34: 180-3, 1992
30. Check J H, et al. Clin Exp Obstet. Gyn. 30, 195-6, 2003
31. Small C M, et al. Epidemiology 17: 52-60, 2006
32. Brodin T, et al. Fert and Steril in press, 2007
33. Boue J, et al., Teratology 12: 11-26, 1975
34. Van Blerkom J, Davis P. Hum. Reprod. 16: 757-64, 2001
35. Lucket D C and Mukherjee A B, J. Hered 1986: 77: 39-42
36. Vogel R, et al., Reprod Toxicol. 1992: 6: 329-33
37. Bernstein, et al., unpublished data
38. Denko N C, et al., Proc. Nat. Acad. Sci. 24: 5124-8, 1994
39. Rao P N and Engelberg J. Exp Cell Res. 48: 71-81, 1967
40. Li, J J., et al., Proc Nat Acad. Sci. 101: 18123-28, 2004
41. Meraldi P, et al., Curr Opin. Genet. Devel. 14: 29-36, 2004
42. Gadea B B, Ruderman J V. Molec Biol. of the Cell 16: 1305-18, 2005
43. Castro A, et al., J. Biol. Chem. 278: 2236-41, 2003
44. Dutertre S, et al., Oncogene 21: 6175-83, 2002
45. Hunt P A, et al., Current Biol. 13: 546-53, 2003
46. Can A, et al., Molec Hum Reprod. 11: 389-96, 2005
47. Can A, Semiz O. Molec Hum. Reprod. 6: 154-62, 2000
48. London S N, et al., Fert. Steril 73: 620-26, 2000
49. Albertini D F, Mutat. Res. 296: 57-68, 1992
50. Plancha C E, Albertini D F. Biol. Reprod. 51: 852-64, 1994
51. Roberts, R, et al., Biol. Reprod. 72: 107-18, 2005
52. Willson J, Obstetric and Gynecol. 8$^{th}$ Ed. C. V. Mosby Co, New York, 1987
53. Gougeon A. Maturitas 30: 137-42, 1998
54. Volarcik K, et al., Hum Reprod. 13: 154-60, 1998
55. Eichenlaub-Ritter, U., et al., Chromosoma 96: 220-6, 1988
56. Eichenlaub-Ritter U, Boll 1. Cytogen Cell Gen. 1989: 52: 170-76
57. Miyamoto et al., J. Exp. Zool 272: 116-22, 1995
58. Braw-Tal R., et al., J. Reprod. Fert. 109: 165-71, 1997
59. Liu L, Keefe D L. Hum Reprod. 17: 2678-85, 2002
60. Liu L and Keefe D, Biol. Reprod. 71: 1724-9, 2004
61. Liu L and J Keefe D. Reprod Biomed Online 16: 103-12, 2008
62. Hovatta O, et al., Hum. Reprod. 12: 1032-6, 1997
63. Scott J E, et al., Reprod. MedOnline 9: 287-93, 2004
64. Welt C K, et al. J. Clin. Endo Metab. 84: 105-111, 1999
65. Trunet P F., et al. J. Clin. Endo Metab. 77: 319-23, 1993
66. Lipton A, et al. Cancer 75: 2132-8, 1995
67. Haynes B P, et al. J. Steroid Biochem Mol. Biol. 87: 35-45, 2003
68. Brown, J B. Aust N Z J Obstet. Gynecol. 18: 47-54, 1978
69. Schoemaker, J, et al. Bailliere's Clinical Obstetrics and Gynecology 7: 297-308, 1993
70. Fatemi H M, et al. Hum Reprod Update 13: 581-90, 2007
71. Oktay K, et al. J. Clin. Endo Metab. 82: 3748-51, 1997

Any patents or publications mentioned in this specification are indicative of the level of those skilled in the art to which the invention pertains. Further, these patents and publications are incorporated by reference herein to the same extent as if each individual publication was specifically and individually incorporated by reference.

One skilled in the art would appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A method for reducing the incidence of infertility by regulating levels of follicle stimulating hormone, luteinizing hormone, estradiol, and progesterone in a woman in need of such treatment, consisting of the steps of:
   a) administering a gonadotropin releasing hormone or an agonist of gonadotropin releasing hormone or an antagonist of gonadotropin releasing hormone during the follicular and luteal phases
      (i) to reduce pituitary secretion of follicle stimulating hormone to about 4.5 IU/L or less and luteinizing hormone to about 5 IU/L or less and,
      (ii) to attenuate ovarian secretion of progesterone and estradiol such that endogenous levels of progesterone are about 5 nmol/L or less and endogenous levels of estradiol are about 150 pmol/L or less;
   b) administering follicle stimulating hormone during the follicular and luteal phases of the menstrual cycles until a pregnancy attempt;
   c) administering luteinizing hormone, human chorionic gonadotropin, progesterone or a combination thereof for luteal phase support,
   d) repeating the steps a) to c) over at least 2 menstrual cycles prior to the pregnancy attempt, wherein said regulating is effective in said woman such that said levels of follicle stimulating hormone become similar to the varying serum levels of follicle stimulating hormone that are specific for each stage of the menstrual cycle in a young, fertile woman during the at least 2 menstrual cycles during which treatment is performed until the pregnancy attempt, thereby reducing the incidence of infertility in said woman.

2. The method of claim 1, wherein said administration of luteinizing hormone and/or human chorionic gonadotropin assists in oocyte and follicular maturation and elicits ovulation.

3. The method of claim 1, wherein said agonist of gonadotropin releasing hormone consists of Leuprolide, Buserelin, Goserelin, Histrelin, Leuprorelin, Nafarelin, Triptorelin, gonadorelin, fertirelin, or deslorelin.

4. The method of claim 1, wherein said antagonist of gonadotropin releasing hormone consists of abarelix, cetrorelix, ganirelix, antarelix, miturelix (antide), Nal-glu, or orgalutran.

5. The method of claim 1, wherein said follicle stimulating hormone is administered as human menopausal gonadotropin, purified follicle stimulating hormone, recombinant follicle stimulating hormone, or a combination thereof.

6. The method of claim 1, wherein said luteal phase progesterone is administered as progesterone in oil for intramuscular injections; micronized progesterone vaginal suppositories in oil consisting of prometrium, uterogestan, minagest or microgest; bioadhesive vaginal gels consisting of crinone or prochieve, with or without supplementation with an oral progesterone preparation consisting of prometrium, uterogestan, minagest or microgest capsules.

7. The method of claim 1, wherein said regulation is effective in normalization of menstrual cycle length, enhancing chances of successful pregnancy in women, reducing infertility by other pathways promoted by hormonal regulation or a combination thereof.

8. The method of claim 7, wherein said normalization of menstrual cycle length restores the duration of the follicular phase of said woman to approximate that of a young fertile woman.

9. The method of claim 8, wherein said normalization is by administration of human menopausal gonadotropin, purified follicle stimulating hormone, and/or recombinant follicle stimulating hormone; supplementation with luteinizing hormone and/or supplementation with urinary hCG, recombinant hCG, or highly purified hCG.

10. The method of claim 1, wherein said infertility is due to premature ovarian failure, repeated implantation failure after in vitro fertilization, diminished ovarian reserve or idiopathic infertility.

11. The method of claim 1, wherein said woman has an elevated follicle stimulating hormone level and a normal estradiol level.

12. A method for reducing the incidence of infertility in a woman having elevated estradiol in need of such a treatment, comprising the steps of:
  a) administering to the woman having elevated estradiol a gonadotropin releasing hormone or an agonist of gonadotropin releasing hormone or an antagonist of gonadotropin releasing hormone during the follicular and luteal phases
    (i) to reduce pituitary secretion of follicle stimulating hormone to about 4.5 IU/L or less and luteinizing hormone to about 5 IU/L or less and,
    (ii) to reduce ovarian secretion of progesterone and estradiol such that endogenous levels of progesterone are about 5 nmol/L or less and endogenous levels of estradiol are about 150 pmol/L or less during the woman's menstrual cycle until a pregnancy attempt;
  b) administering follicle stimulating hormone during the follicular and luteal phases of the woman's menstrual cycles to approximate the varying serum levels of follicle stimulating hormone that are specific for each stage of a menstrual cycle in a young and fertile woman during the woman's menstrual cycles until the pregnancy attempt;
  c) administering luteinizing hormone or human chorionic gonadotropin to support follicular and oocyte maturation, to trigger ovulation, and to support the luteal phase, or administering progesterone to support the luteal phase in said woman, or administering a combination thereof;
  d) administering an inhibitor of the enzyme aromatase to the woman having elevated estradiol; and
  e) repeating the steps a) to d) during at least 2 menstrual cycles prior to the pregnancy attempt to regulate the level of estradiol in said woman such that said level approximates the level of estradiol of a young and fertile woman throughout the menstrual cycles, thereby reducing the incidence of infertility in said woman.

13. The method of claim 12, wherein estradiol is restored at a level that is specific for each stage of the menstrual cycle, LH activity is restored in quantities sufficient to trigger ovulation in mid-cycle, and progesterone supports the luteal phase at levels that are adequate for the luteal phase.

14. The method of claim 12, wherein said against of gonadotropin releasing hormone consists of Leuprolide, Buserelin, Goserelin, Histrelin, Leuprorelin, Nafarelin, Triptorelin, gonadorelin, fertirelin, or deslorelin.

15. The method of claim 12, wherein said antagonist of gonadotropin releasing hormone consists of abarelix, cetrorelix, ganirelix, antarelix, iturelix (antide), Nal-glu, or orgalutran.

16. The method of claim 12, wherein said follicle stimulating hormone is human menopausal gonadotropin or urofollitropin, recombinant follicle stimulating hormone, or a combination thereof.

17. The method of claim 12, wherein said progesterone is administered as progesterone in oil for intramuscular injections; micronized progesterone vaginal suppositories in oil consisting of prometrium, uterogestan, minagest or microgest; bioadhesive vaginal gels consisting of crinone or prochieve, with or without supplementation with an oral progesterone preparation consisting of prometrium, uterogestan, minagest or microgest capsules.

18. The method of claim 12, wherein said aromatase inhibitor is aminogluthetimide, anastrozole, exemestane, formestane, letrozole, vorozole, 4-androstene-3,6,17-trione, 1,4,6-androstatrien-3,17-dione, or testolactone.

19. The method of claim 12, wherein said regulation is effective in normalization of menstrual cycle length, enhancing chances of successful pregnancy without miscarriage in women with or without elevated estradiol, reducing infertility by other pathways regulated by hormonal levels or a combination thereof.

20. The method of claim 19, wherein said normalization of menstrual cycle length restores the duration of the follicular phase of said woman to approximate that of a young and fertile woman.

21. The method of claim 20, wherein said normalization is by administration of human menopausal gonadotropin, purified follicle stimulating hormone, recombinant follicle stimulating hormone; supplementation with luteinizing hormone; supplementation with hCG; triggering of ovulation with urinary hCG, highly purified hCG, recombinant hCG, recombinant LH or a combination thereof.

22. The method of claim 12, wherein said infertility is due to premature ovarian failure, repeated implantation failure after in vitro fertilization, ovarian aging, diminished ovarian reserve or idiopathic infertility.

23. The method of claim 12, wherein said woman has elevated follicle stimulating hormone level and elevated estradiol level or has normal follicle stimulating hormone level and elevated estradiol level.

* * * * *